US010697028B2

(12) United States Patent
Curtis et al.

(10) Patent No.: US 10,697,028 B2
(45) Date of Patent: Jun. 30, 2020

(54) DETECTION OF HIV-1 NUCLEIC ACIDS BY REVERSE-TRANSCRIPTION LOOP-MEDIATED ISOTHERMAL AMPLIFICATION

(71) Applicant: The United States of America as represented by the Secretary, Department of Health and Human Services, Bethesda, MD (US)

(72) Inventors: Kelly A. Curtis, Atlanta, GA (US); Sherry M. Owen, Atlanta, GA (US); Philip Niedzwiedz, Atlanta, GA (US); Donna L. Rudolph, Atlanta, GA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 417 days.

(21) Appl. No.: 15/524,209

(22) PCT Filed: Oct. 28, 2015

(86) PCT No.: PCT/US2015/057861
§ 371 (c)(1),
(2) Date: May 3, 2017

(87) PCT Pub. No.: WO2016/073255
PCT Pub. Date: May 12, 2016

(65) Prior Publication Data
US 2019/0093181 A1 Mar. 28, 2019

Related U.S. Application Data

(60) Provisional application No. 62/076,334, filed on Nov. 6, 2014.

(51) Int. Cl.
*C12Q 1/70* (2006.01)
*C12Q 1/6853* (2018.01)
*C12Q 1/6876* (2018.01)

(52) U.S. Cl.
CPC .......... *C12Q 1/703* (2013.01); *C12Q 1/6853* (2013.01); *C12Q 1/6876* (2013.01); *C12Q 2600/16* (2013.01)

(58) Field of Classification Search
None
See application file for complete search history.

(56) References Cited

U.S. PATENT DOCUMENTS 6,001,558 A * 12/1999 Backus .................. C12Q 1/703
435/5
2004/0023207 A1 * 2/2004 Polansky ............... A61K 31/00
435/5

FOREIGN PATENT DOCUMENTS

WO    WO-9904011 A2 *  1/1999  .......... C07K 14/005
WO    WO 2009/108693    9/2009

OTHER PUBLICATIONS

GenBank AJ564930 [online] Jul. 26, 2016 [retrieved on Jun. 23, 2019] retrieved from https://www.ncbi.nlm.nih.gov/nuccore/aj564930 (Year: 2016).*
Curtis et al., "Rapid detection of HIV-1 by reverse-transcription, loop-mediated isothermal amplification (RT-LAMP)," *Journal of Virological Methods*, vol. 151, pp. 264-270, 2008.
Curtis et al., "Sequence-specific detection method for reverse transcription, loop-mediated isothermal amplification of HIV-1," *Journal of Medical Virology*, vol. 81, pp. 966-972, 2009.
Curtis et al., "Isothermal amplification using a chemical heating device for point-of-care detection of HIV-1," *PLoS One*, 7:e31432, 2012 (6 pages).
Ferns et al., "Development and evaluation of a real-time RT-PCR assay for quantification of cell-free human immunodeficiency virus type 2 using a Brome Mosaic Virus internal control," *Journal of Virological Methods*, vol. 135, pp. 102-108, 2006.
Hosaka et al., "Rapid detection of human immunodeficiency virus type 1 group M by a reverse transcription-loop-mediated isothermal amplification assay," *Journal of Virological Methods*, vol. 157, pp. 195-199, 2009.
Myers et al., "A handheld point-of-care genomic diagnostic system, " *PLOS ONE*, 8:e70266, 2013 (9 pages).
Nagamine et al., "Accelerated reaction by loop-mediated isothermal amplification using loop primers," *Molecular and Cellular Probes*, vol. 16, pp. 223-229, 2002.
Notomi et al., "Loop-mediated isothermal amplification of DNA," *Nucleic Acids Research*, 28:E63, 2000 (7 pages).
Zeng et al., "Rapid quantitative detection of Human immunodeficiency virus type 1 by a reverse transcription-loop-mediated isothermal amplification assay," *Gene*, vol. 541, pp. 123-128, 2014.
Zhao et al., "Development and evaluation of reverse-transcription loop-mediated isothermal amplification for rapid detection of human immunodeficiency virus type 1," *Indian Journal of Medical Microbiology*, vol. 30, No. 4, pp. 391-396, 2012.

* cited by examiner

*Primary Examiner* — Samuel C Woolwine
(74) *Attorney, Agent, or Firm* — Klarquist Sparkman, LLP

(57) ABSTRACT

Disclosed herein are methods of detecting HIV-1 nucleic acids in a sample (such as from a sample containing or suspected to contain HIV-1 nucleic acid). In some examples, the methods include loop-mediated isothermal amplification (LAMP) or reverse transcription-LAMP (RT-LAMP). In some examples, the methods include contacting a sample with one or more sets of LAMP primers specific for HIV-1 (such as LAMP primers specific for an HIV-1 integrase nucleic acid or LAMP primers specific for an HIV-1 reverse transcriptase nucleic acid) under conditions sufficient to produce an amplification product and detecting the amplification product. Sets of LAMP primers for detection of HIV-1 integrase nucleic acids (such as SEQ ID NOs: 8-14 or 8-27) and HIV-1 reverse transcriptase nucleic acids (such as SEQ ID NOs: 1-7) are provided herein.

35 Claims, 1 Drawing Sheet
Specification includes a Sequence Listing.

DNA

RNA

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 1 agttcccctta gataaagact t                                              21

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 2
cctacataca aatcatccat gt                                              22

<210> SEQ ID NO 3
<211> LENGTH: 51
<212> TYPE: DNA
<213> ORGANISM: Artificial Sequence
<220> FEATURE:
<223> OTHER INFORMATION: Synthetic oligonucleotide primer

<400> SEQUENCE: 3
gtggaagcac attgtactga tatcttttg gaagtatact gcatttacca t              51

<210> SEQ ID NO 4
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 4
ggaaaggatc accagcaata ttcctctgga ttttgttttc taaaaggc                 48

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 5
ggtgtctcat tgtttatact a                                              21

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 6
gcatgacaaa aatcttaga                                                 19

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 7
aaacaatgag acacc                                                     15

<210> SEQ ID NO 8

```
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
ggtttattac agggacagca                                                    20

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 9
atcctgtcta cttgccac                                                      18

<210> SEQ ID NO 10
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 10
cttgtattac tactgcccct tcacgatcca ctttggaaag gacc                         44

<210> SEQ ID NO 11
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 11
tgacataaaa gtagtgccaa gaagatttta caatcatcac ctgccatc                     48

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
ctttccagag aagctttgct                                                    20

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 13
agcaaagatc attagggatt at                                                 22

<210> SEQ ID NO 14
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 14
```

```
taatgatctt tgct                                              14
```

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 15

```
atcctgtcta cctgccac                                          18
```

<210> SEQ ID NO 16
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 16

```
cttgtattac tactgcccct tcacgaycca atttggaaag gacc             44
```

<210> SEQ ID NO 17
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 17

```
cttgtattac tactgcccct tcacgaccct atttggaaag gacc             44
```

<210> SEQ ID NO 18
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 18

```
tgatataaar gtagtaccaa gaagatttta caatcatcac ctgccatc         48
```

<210> SEQ ID NO 19
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 19

```
tgacataaag gtagtaccaa ggaggtttta caatcagcac ctgccatc         48
```

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 20

```
ctttccagag tagttttgct                                        20
```

<210> SEQ ID NO 21
<211> LENGTH: 22
<212> TYPE: DNA

<213> ORGANISM: Artificial Sequence
<220> FEATURE:
<223> OTHER INFORMATION: Synthetic oligonucleotide primer

<400> SEQUENCE: 21
agtaaaaatc attaaggact at                                          22

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 22
agcaaaaatc attaaggatt at                                          22

<210> SEQ ID NO 23
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 23
taatgatctt tgct                                                   14

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 24
atagtcctta atgattttta ct                                          22

<210> SEQ ID NO 25
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 25
ccttaatgat ttttact                                                17

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 26
ataatcctta atgatttttg ct                                          22

<210> SEQ ID NO 27
<211> LENGTH: 17
<212> TYPE: DNA
<213> ORGANISM: Artificial Sequence
<220> FEATURE:

-continued

```
<223> OTHER INFORMATION: Synthetic oligonucleotide primer

<400> SEQUENCE: 27
ccttaatgat ttttgct                                                    17
```

DETECTION OF HIV-1 NUCLEIC ACIDS BY REVERSE-TRANSCRIPTION LOOP-MEDIATED ISOTHERMAL AMPLIFICATION

CROSS REFERENCE TO RELATED APPLICATIONS

This is the U.S. National Stage of International Application No. PCT/US2015/057861, filed Oct. 28, 2015, which was published in English under PCT Article 21(2), which in turn claims the benefit of U.S. Provisional Application No. 62/076,334, filed Nov. 6, 2014. The provisional application is incorporated herein in its entirety.

FIELD

This disclosure relates to human immunodeficiency virus (HIV), particularly methods of amplifying or detecting HIV-1 nucleic acids and compositions for use in said methods.

BACKGROUND

Routine diagnostic testing is imperative for the early detection and treatment of HIV infection. Because individuals are at higher risk for transmitting the virus during early or acute infection, accurate and timely diagnosis may reduce the transmission of HIV when the individual is most infectious (Wawer et al., *J. Inf. Dis.* 191:1403-1409, 2005). Early detection of HIV has been shown to lead to reduced high-risk behavior and to connect individuals to treatment earlier, which can reduce transmissible virus (Branson et al., *Morbidity and Mortality Weekly Report* 55:1-17, 2006; Marks et al., *J. Acquired Immune Deficiency Syndromes* 39:446-453, 2005). Although there are currently several FDA-approved HIV diagnostic tests available, there are still 1.1 million people in the U.S. living with HIV, of which 15.8% are undiagnosed or unaware of their infection status (*CDC HIV Surveillance Report*, 18:1-47, 2011).

For accurate and early detection of HIV-1, as well as HIV-2, a revised HIV laboratory testing algorithm has been developed. In this algorithm, specimens are screened with a sensitive HIV-1/2 immunoassay, preferably a fourth-generation antigen/antibody assay, followed by an HIV-1/2 differentiation assay. Specimens that are non-reactive are considered negative. Specimens that have concordant reactivity on the screening and supplemental test are considered positive for HIV-1/2 antibodies; however, in the case of discordant immunoassay results, HIV-1 nucleic acid amplification testing (NAAT) is recommended. NAAT generally is highly sensitive, virus-specific, and allows for detection of infection approximately two weeks earlier than most antibody-based tests (Schito et al., *J. Inf. Dis.* 201(Suppl. 1):S1-6, 2010).

To date, there are no definitive guidelines for HIV testing at the point-of-care (POC). POC testing has increased the number of individuals who are screened for HIV and receive their HIV test results (Schito et al., *J. Inf. Dis.* 201(Suppl. 1):S1-6, 2010). Rapid tests have facilitated HIV testing at the POC because they can be completed in a short period of time (typically 30-60 minutes) and require minimal technical expertise. Currently, there are a number of rapid antibody tests available that are FDA-approved; however, they are not as sensitive for detection of early HIV infection as most are laboratory-based assays and remain negative during the post-infection, but pre-seroconversion period (Wesolowski et al., *J. Clin. Virol.* 58:240-244, 2014).

SUMMARY

The availability of a highly sensitive and specific rapid NAAT for use at the POC would increase the ability to detect acute infection. Desirable or advantageous characteristics for a rapid NAAT include completion in a short time frame with a few simple steps, ease of interpretation, and no or minimal equipment required (particularly no or minimal specialized equipment). In addition, the rapid NAAT ideally exhibits a high degree of sensitivity and specificity. Isothermal amplification techniques are attractive for the development of a rapid NAAT because they do not require thermal cycling, and the reaction can therefore be run in a simple heat block, water bath, or other portable heating device. Loop-mediated isothermal amplification (LAMP) or reverse transcription-LAMP (RT-LAMP) are examples of such an isothermal amplification technique. The availability of a rapid NAAT, such as the HIV-1 RT-LAMP assays described herein, improves the diagnosis of acutely infected individuals, who might otherwise be missed by current rapid antibody tests.

Disclosed herein are methods of detecting HIV-1 nucleic acids in a sample (such as from a sample containing or suspected to contain HIV-1 nucleic acid). In some examples, the methods include LAMP or RT-LAMP. The disclosed assays are advantageous because they provide high specificity (due to the use of a set of primers that hybridize to multiple sequences in the same target region). The method can also be performed without extraction of nucleic acids (for example, using whole blood, plasma, or saliva directly). The disclosed RT-LAMP assays are also rapid, require minimal laboratory equipment (a heat block, water bath, or chemical heater), and the methods can incorporate fluorescent detection methods for real-time or immediate naked-eye detection (for example, with a hand-held ultraviolet light), facilitating use at POC. Finally, the disclosed methods provide early detection and/or diagnosis of HIV-1, for example up to 24 days earlier than a representative rapid antibody test.

In some examples, the methods include contacting a sample with one or more sets of LAMP primers specific for HIV-1 (such as a set of LAMP primers specific for an HIV-1 integrase (INT) nucleic acid and/or a set of LAMP primers specific for an HIV-1 reverse transcriptase (RT) nucleic acid) under conditions sufficient to produce an amplification product, and detecting the amplification product. In some examples, the method includes contacting the sample with a set of LAMP primers specific for HIV-1 INT such as a set of primers of SEQ ID NOs: 8-14 or a set of primers of SEQ ID NOs: 8-27. In another example, the method includes contacting the sample with a set of LAMP primers specific for HIV-1 INT, such as a set of primers of SEQ ID NOs: 8, 9, 12-23, 25, and optionally 27. In additional examples, the method further includes contacting the sample with a set of LAMP primers specific for HIV-1 RT, such as a set of primers of SEQ ID NOs: 1-7.

Sets of LAMP primers for detection of HIV-1 integrase nucleic acids (such as SEQ ID NOs: 8-14, SEQ ID NOs: 8-27, or SEQ ID NOs: 8, 9, 12-23, 25, and optionally 27) and HIV-1 reverse transcriptase nucleic acids (such as SEQ ID NOs: 1-7) are also provided herein. Also disclosed are kits including one or more of sets of LAMP primers (such as a set of HIV-1 INT LAMP primers described herein).

The foregoing and other features of the disclosure will become more apparent from the following detailed description, which proceeds with reference to the accompanying figures.

SEQUENCE LISTING

Figure 1A:
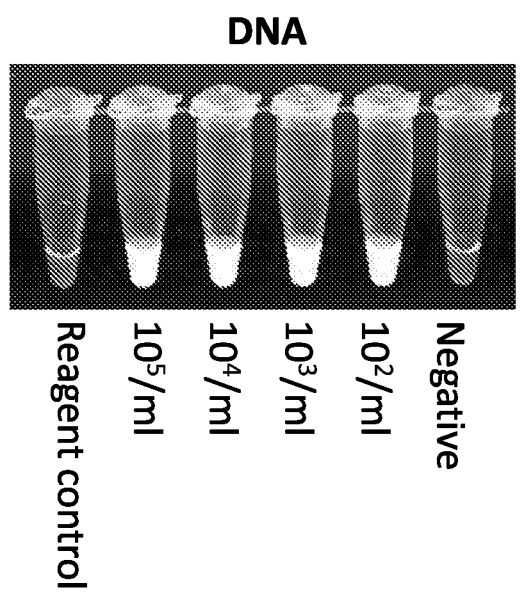
FIGS. 1A and 1B are a pair of images showing HIV-1 INT RT-LAMP sensitivity. The RT-LAMP reaction tubes were observed under UV light. Representative tubes for amplification of DNA (FIG. 1A) and RNA (FIG. 1B) are shown.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NOs: 1-7 are nucleic acid sequences of exemplary HIV-1 reverse transcriptase RT-LAMP primers.

SEQ ID NOs: 8-27 are nucleic acid sequences of exemplary HIV-1 INT RT-LAMP primers.

DETAILED DESCRIPTION

I. Terms

Unless otherwise noted, technical terms are used according to conventional usage. Definitions of common terms in molecular biology may be found in Lewin's Genes X, ed. Krebs et al, Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Réclei, *Encyclopedic Dictionary of Genetics, Genomics, Proteomics and Informatics*, 3rd Edition, Springer, 2008 (ISBN: 1402067534).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with the GenBank Accession Nos. or HIV Database Accession Nos. mentioned herein are incorporated by reference in their entirety as were present on Nov. 6, 2014, to the extent permissible by applicable rules and/or law. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of this disclosure, the following explanations of specific terms are provided:

Amplification: Increasing the number of copies of a nucleic acid molecule, such as a gene or fragment of a gene, for example at least a portion of an HIV nucleic acid molecule. The products of an amplification reaction are called amplification products. An example of in vitro amplification is the polymerase chain reaction (PCR), in which a sample (such as a biological sample from a subject) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include real-time PCR, quantitative real-time PCR (qPCR), reverse transcription PCR (RT-PCR), quantitative RT-PCR (qRT-PCR), loop-mediated isothermal amplification (LAMP; see Notomi et al., *Nucl. Acids Res.* 28:e63, 2000); reverse-transcription LAMP (RT-LAMP); strand displacement amplification (see U.S. Pat. No. 5,744,311); transcription-mediated amplification (U.S. Pat. No. 5,399,491) transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Conditions sufficient for: Any environment that permits the desired activity, for example, that permits specific binding or hybridization between two nucleic acid molecules or that permits reverse transcription and/or amplification of a nucleic acid. Such an environment may include, but is not limited to, particular incubation conditions (such as time and or temperature) or presence and/or concentration of particular factors, for example in a solution (such as buffer(s), salt(s), metal ion(s), detergent(s), nucleotide(s), enzyme(s), and so on).

Contact: Placement in direct physical association; for example in solid and/or liquid form. For example, contacting can occur in vitro with one or more primers and/or probes and a biological sample (such as a sample including nucleic acids) in solution.

Detectable label: A compound or composition that is conjugated directly or indirectly to another molecule (such as a nucleic acid molecule) to facilitate detection of that molecule. Specific non-limiting examples of labels include fluorescent and fluorogenic moieties (e.g., fluorophores), chromogenic moieties, haptens (such as biotin, digoxigenin, and fluorescein), affinity tags, and radioactive isotopes (such as $^{32}P$, $^{33}P$, $^{35}S$, and $^{125}I$). The label can be directly detectable (e.g., optically detectable) or indirectly detectable (for example, via interaction with one or more additional molecules that are in turn detectable). Methods for labeling nucleic acids, and guidance in the choice of labels useful for various purposes, are discussed, e.g., in Sambrook and Russell, in *Molecular Cloning: A Laboratory Manual*, 3rd Ed., Cold Spring Harbor Laboratory Press (2001) and Ausubel et al., in *Current Protocols in Molecular Biology*, Greene Publishing Associates and Wiley-Intersciences (1987, and including updates).

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes and primers disclosed herein are known to those of skill in the art and include 4-acetamido-4'-isothiocyanatostilbene-2,2'disulfonic acid; acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcoulnarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), 6-carboxy-fluorescein (HEX), and TET (tetramethyl fluorescein); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate, and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® (Applied Biosystems); LC Red 640; LC Red 705; and Yakima yellow amongst others. Additional examples of fluorophores include Quasar® 670, Quasar® 570, CalRed 590, CalRed 610, CalRed615, CalRed 635, CalGreen 520, CalGold 540, and CalOrange 560 (Biosearch Technologies, Novato, Calif.). One skilled in the art can select additional fluorophores, for example those available from Molecular Probes/ Life Technologies (Carlsbad, Calif.).

In particular examples, a fluorophore is used as a donor fluorophore or as an acceptor fluorophore. "Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Biosearch Technologies; such as BHQ0, BHQ1, BHQ2, and BHQ3), ECLIPSE™ Dark Quencher (Epoch Biosciences), or IOWA BLACK™ (Integrated DNA Technologies). A quencher can reduce or quench the emission of a donor fluorophore.

"Donor Fluorophores" are fluorophores or luminescent molecules capable of transferring energy to an acceptor fluorophore, in some examples generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Isolated: An "isolated" biological component (such as a nucleic acid) has been substantially separated or purified away from other biological components in which the component naturally occurs, such as other chromosomal and extrachromosomal DNA, RNA, and proteins. Nucleic acids that have been "isolated" include nucleic acids purified by standard purification methods. The term also embraces nucleic acids prepared by recombinant expression in a host cell as well as chemically synthesized nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Human immunodeficiency virus (HIV): HIV is a retrovirus that causes immunosuppression in humans (HIV disease), and leads to disease states known as acquired immunodeficiency syndrome (AIDS) and AIDS related complex (ARC). "HIV disease" refers to a well-recognized constellation of signs and symptoms (including the development of opportunistic infections) in persons who are infected by an HIV virus, as determined by antibody or western blot studies or detection of HIV nucleic acids. Laboratory findings associated with this disease are a progressive decline in T cells. HIV includes HIV type 1 (HIV-1) and HIV type 2 (HIV-2). Related viruses that are used as animal models include simian immunodeficiency virus (SIV) and feline immunodeficiency virus (FIV). HIV nucleic acid and protein sequences are available in public databases, including GenBank and the HIV Database (available on the World Wide Web at hiv.lanl.gov). Exemplary reference sequences include HXB2 for HIV-1 (e.g., GenBank Accession Nos.

AF033819, K03455 or M38432) and MAC239 for HIV-2 (GenBank Accession No. M33262), all of which are incorporated herein by reference in their entirety, as included in GenBank on Nov. 6, 2014.

The HIV genome contains three major genes, gag, pol, and env, which encode major structural proteins and essential enzymes. The gag gene encodes the Gag polyprotein, which is processed to six protein products. The pol gene encodes the Pol polyprotein, which is processed to produce reverse transcriptase (RT), RNase H, integrase (INT), and protease (PRO). Env encodes gp160, which is processed to the two envelope proteins, gp120 and gp41. In addition to these, HIV has two regulatory proteins (Tat and Rev) and accessory proteins (Nef, Vpr, Vif and Vpu). Each end of the HIV provirus has a repeated sequence referred to as a long terminal repeat (LTR).

There are four HIV-1 groups—M ("major"), O ("outlier"), N, and P. The majority of HIV-1 infections are group M. There are at least nine subtypes (clades) of HIV-1 in group M, known as subtypes A, B, C, D, F, G, H, J, and K. There are also two hybrid or recombinant subtypes, A/E (also referred to as AE) and A/G (also referred to as AG). The different subtypes are generally geographically localized; however, they are becoming more widely distributed globally.

Loop-mediated isothermal amplification (LAMP): A method for amplifying DNA. The method is a single-step amplification reaction utilizing a DNA polymerase with strand displacement activity (e.g., Notomi et al., *Nucl. Acids. Res.* 28:E63, 2000; Nagamine et al., *Mol. Cell. Probes* 16:223-229, 2002; Mori et al., *J. Biochem. Biophys. Methods* 59:145-157, 2004). At least four primers, which are specific for eight regions within a target nucleic acid sequence, are typically used for LAMP. The primers include a forward outer primer (F3), a backward outer primer (B3), a forward inner primer (HP), and a backward inner primer (BIP). A forward loop primer (Loop F), and a backward loop primer (Loop B) can also be included in some embodiments. The amplification reaction produces a stem-loop DNA with inverted repeats of the target nucleic acid sequence. Reverse transcriptase can be added to the reaction for amplification of RNA target sequences. This variation is referred to as RT-LAMP.

Primer: Primers are short nucleic acids, generally DNA oligonucleotides 10 nucleotides or more in length (such as 10-60, 15-50, 20-45, or 20-40 nucleotides in length). Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR), LAMP, RT-LAMP, or other nucleic acid amplification methods known in the art.

Probe: A probe typically comprises an isolated nucleic acid (for example, at least 10 or more nucleotides in length) with an attached detectable label or reporter molecule. Typical labels include radioactive isotopes, ligands, chemiluminescent agents, fluorophores, and enzymes. Methods for labeling oligonucleotides and guidance in the choice of labels appropriate for various purposes are discussed, e.g., in Sambrook et al. (2001) and Ausubel et al. (1987).

Recombinant nucleic acid: A nucleic acid molecule that is not naturally occurring or has a sequence that is made by an artificial combination of two otherwise separated segments of nucleotide sequence. This artificial combination is accomplished by chemical synthesis or by the artificial manipulation of isolated segments of nucleic acids, e.g., by genetic engineering techniques such as those described in Sambrook and Russell, in *Molecular Cloning: A Laboratory Manual*, 3$^{rd}$ Ed., Cold Spring Harbor Laboratory Press (2001). The term "recombinant" includes nucleic acids that have been altered solely by addition, substitution, or deletion of a portion of a natural nucleic acid molecule. A recombinant nucleic acid also includes a heterologous nucleic acid that is inserted in a vector. A "heterologous nucleic acid" refers to a nucleic acid that originates from a different genetic source or species, for example a viral nucleic acid inserted in a bacterial plasmid (referred to herein in some examples as a recombinant vector).

Sample (or biological sample): A biological specimen containing DNA (for example, genomic DNA or cDNA), RNA (including mRNA), protein, or combinations thereof. Examples include, but are not limited to isolated nucleic acids, cells, cell lysates, chromosomal preparations, peripheral blood, urine, saliva, tissue biopsy (such as a tumor biopsy or lymph node biopsy), surgical specimen, bone marrow, amniocentesis samples, and autopsy material. In one example, a sample includes viral nucleic acids, for example, HIV RNA or DNA reverse transcribed from HIV RNA. In particular examples, samples are used directly (e.g., fresh or frozen), or can be manipulated prior to use, for example, by fixation (e.g., using formalin) and/or embedding in wax (such as FFPE tissue samples).

Subject: Any multi-cellular vertebrate organism, such as human and non-human mammals (including non-human primates). In one example, a subject is known to be or is suspected of being infected with HIV.

II. Methods of Detecting HIV-1 Nucleic Acids

Disclosed herein are methods of detecting HIV-1 nucleic acids in a sample (such as in a sample from a subject infected with or suspected to be infected with HIV-1). The disclosed methods can be used to diagnose an infection with HIV-1 in a subject, for example, by analyzing a biological sample from a subject to detect HIV-1 nucleic acids in the sample from the subject. In some examples, the methods include LAMP or RT-LAMP assays. In particular examples, the methods include detecting HIV-1 subtypes, including Group M subtypes (such as subtypes A, B, C, D, AE, and AG).

The methods described herein may be used for any purpose for which detection of HIV nucleic acids, such as HIV-1 nucleic acids, is desirable, including diagnostic and prognostic applications, such as in laboratory and clinical settings. Appropriate samples include any conventional biological samples, including clinical samples obtained from a human or veterinary subject. Suitable samples include all biological samples useful for detection of infection in subjects, including, but not limited to, cells (such as buccal cells or peripheral blood mononuclear cells), tissues, autopsy samples, bone marrow aspirates, bodily fluids (for example, blood, serum, plasma, urine, cerebrospinal fluid, middle ear fluids, breast milk, bronchoalveolar lavage, tracheal aspirates, sputum, oral fluids, nasopharyngeal aspirates, oropharyngeal aspirates, or saliva), oral swabs, eye swabs, cervical swabs, vaginal swabs, rectal swabs, stool, and stool suspensions. The sample can be used directly or can be processed, such as by adding solvents, preservatives, buffers, or other compounds or substances. In some examples, nucleic acids are isolated from the sample. In other examples, isolation of nucleic acids from the sample is not necessary prior to use in the methods disclosed herein and the sample (such as a blood sample) is used directly or with minimal pre-processing. For example, bodily fluids (such as blood or plasma) can in some examples be diluted in water or buffer and used in the disclosed RT-LAMP assays without additional processing. In some examples, the sample (for example, a sample containing cells, such as peripheral blood mononuclear cells) is pre-treated to lyse cells (for example with a lysis buffer), but nucleic acids are not isolated prior to use in the RT-LAMP assay.

Samples also include isolated nucleic acids, such as DNA or RNA isolated from a biological specimen from a subject, an HIV isolate, or other source of nucleic acids. Methods for extracting nucleic acids such as RNA and/or DNA from a sample are known to one of skill in the art; such methods will depend upon, for example, the type of sample in which the nucleic acid is found. Nucleic acids can be extracted using standard methods. For instance, rapid nucleic acid preparation can be performed using a commercially available kit (such as kits and/or instruments from Qiagen (such as DNEasy® or RNEasy® kits), Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987).

The disclosed methods are highly sensitive and/or specific for detection of HIV-1 nucleic acids. In some examples, the disclosed methods can detect presence of at least 10 copies of HIV-1 nucleic acids (for example at least $10^2$, $10^3$, $10^4$, $10^5$, $10^6$, $10^7$, or more copies of HIV-1 nucleic acids) in a sample or a particular reaction volume (such as per ml reaction). In particular, non-limiting examples, the disclosed methods have a limit of detection of about $10^2$-$10^3$ copies/ml for HIV-1 DNA and about $10^4$-$10^5$ copies/ml for HIV-1 RNA. However, one of ordinary skill in the art will recognize that the limit of detection of an assay depends on many factors (such as reaction conditions, amount and quality of starting material, and so on) and the limit of detection using particular LAMP primer sets, such as those disclosed herein, may be even less with modifications to the assay conditions.

One advantage of the disclosed methods is that they can detect presence of HIV in a sample (for example, diagnose an HIV-1 infection) at an earlier time point in the course of infection than many currently available HIV-1 testing methods. In some examples, the disclosed HIV-1 INT RT-LAMP assay can detect presence of HIV-1 in a sample at least 1 day sooner (for example at least 2, 3, 4, 5, 6, 7, 10, 14, 21, 28, or more days sooner) than an HIV-1 immunoassay, for example, prior to seroconversion. Exemplary HIV-1 immunoassays include Multispot HIV-1/HIV-2 Rapid Test (Bio-Rad, Redmond, Calif., also referred to herein as "rapid Ab"), GS HIV-1 Western blot (Bio-Rad, also referred to herein as "WB"), third-generation GS HIV-1/HIV-2 Plus 0 EIA (Bio-Rad, also referred to herein as "Ab EIA"), fourth-generation GS HIV Combo Ag/Ab EIA (Bio-Rad, also referred to herein as "Ab+Ag EIA"). In other examples, the disclosed HIV-1 INT RT-LAMP assay can detect HIV-1 nucleic acid in a sample at least 1 day sooner (for example at least 2, 3, 4, 5, 6, 7, or more days sooner) than a different HIV-1 nucleic acid-based assay. In other examples, the disclosed HIV-1 INT RT-LAMP assay does not detect HIV-1 nucleic acid in a sample sooner than a different HIV-1 nucleic acid based assay, but detects HIV-1 nucleic acid in a smaller sample volume (for example 10 µl of extracted nucleic acids or 2.5 µl of specimen in the disclosed assays, as compared to 500 µl of specimen in the APTIMA assay). An exemplary HIV-1 nucleic acid-based assay is the APTIMA HIV-1 qualitative RNA assay (Hologic (Gen-Probe), Bedford, Mass.).

In some examples, the disclosed methods can predict with a sensitivity of at least 90% and a specificity of at least 90% for presence of an HIV-1 nucleic acid (such as an HIV-1 INT nucleic acid and/or an HIV-1 RT nucleic acid), such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

Disclosed herein are methods for detecting HIV-1 in a sample utilizing LAMP or RT-LAMP methods of amplification and detection. LAMP, which was first described by Notomi et al. (*Nucl. Acids Res.* 28:e63, 2000), is a one-step isothermal amplification method that can produce amplified nucleic acids in a short period of time using a DNA polymerase with strand displacement activity. LAMP can be adapted for amplification of RNA targets with the addition of reverse transcriptase (RT) to the reaction without an additional heat step (referred to as RT-LAMP). The isothermal nature of LAMP and RT-LAMP allows for assay flexibility because it can be used with simple and inexpensive heating devices, which can facilitate HIV detection in settings other than centralized clinical laboratories, including at the point-of-care (POC). POC testing is particularly important for HIV diagnosis, as it has the potential to reduce loss to follow-up and to increase the number of individuals that become aware of their HIV status (for example, at the time of their visit). In addition, LAMP and RT-LAMP offer versatility in terms of specimen type and is believed to increase the probability of detecting an amplifiable target in whole blood specimens or dried blood spots.

LAMP or RT-LAMP can also be multiplexed through the addition of multiple LAMP primer sets with different specificities. This capability is advantageous, for example, because it allows for incorporation of internal control(s), amplification of two or more regions within the same target, or detection of two or more targets or pathogens in a single reaction. In some examples, the disclosed methods include a multiplex LAMP or RT-LAMP assay for detection of HIV-1 INT nucleic acids and HIV-1 RT nucleic acids in a single reaction. Multiplex assays may be advantages in at least some embodiments, because detection of clinical isolates may be facilitated by targeting at least two separate, conserved regions within the HIV genome because of the sequence diversity of HIV-1.

In some embodiments, the methods include contacting a sample (such as a sample including or suspected to include HIV-1 nucleic acids) with at least one set of LAMP primers, such as a set of LAMP primers specific for an HIV-1 INT nucleic acid (for example, a set of primers including the sequences of SEQ ID NOs: 8-11, 8-13, or 8-14) under conditions sufficient for amplification of the HIV-1 INT nucleic acid, producing an amplification product. In other embodiments, the methods include contacting a sample with at least one set of LAMP primers specific for an HIV-1 INT nucleic acid under conditions sufficient for amplification of the HIV-1 INT nucleic acid, where the set of LAMP primers includes SEQ ID NO: 8, SEQ ID NO: 9, at least one of SEQ ID NOs: 16 and 17, at least one of SEQ ID NO:s 18 and 19, SEQ ID NO: 12, SEQ ID NO: 13, and at least one of SEQ ID NOs: 14 and 23-27. In another example, the methods include contacting a sample with at least one set of LAMP primers specific for an HIV-1 INT nucleic acid under conditions sufficient for amplification of the HIV-1 INT nucleic acid, where the set of LAMP primers includes SEQ ID NO: 8, SEQ ID NO: 9, SEQ ID NO: 15, SEQ ID NO: 16, SEQ ID NO: 17, SEQ ID NO: 18, SEQ ID NO: 19, SEQ ID NO: 12, SEQ ID NO: 20, SEQ ID NO: 13, SEQ ID NO: 21, SEQ ID NO: 22, SEQ ID NO: 14 (SEQ ID NO: 23), SEQ ID NO: 25, and SEQ ID NO 27. In still further examples, the methods include contacting a sample with at least one set of LAMP primers specific for an HIV-1 INT nucleic acid under conditions sufficient for amplification of the HIV-1 INT nucleic acid, where the set of LAMP primers includes at least one F3 primer, at least one B3 primer, at least one FIP primer, at least one BIP primer, at least one Loop F primer, at least one Loop B primer, and at least one quencher selected from the primers of SEQ ID NOs: 27. In some examples, the set of LAMP primers includes all of SEQ ID NOs: 8-27. In some examples, the set of LAMP primers amplify an HIV-1 INT nucleic acid having at least 80% sequence identify (such as at least 85%, 90%, 95%, 98%, or more sequence identity) to nucleotides 4901-5087 of the HXB2 reference sequence (e.g. GenBank Accession No. AF033819, incorporated herein by reference as present in GenBank on Nov. 6, 2014), or a portion thereof.

In other embodiments, the methods include contacting a sample (such as a sample including or suspected to include HIV-1 nucleic acids) with at least one set of LAMP primers specific for an HIV-1 RT nucleic acid (for example, a set of primers including the sequences of SEQ ID NOs: 1-4, 1-6, or 1-7) under conditions sufficient for amplification of the HIV-1 RT nucleic acid, producing an amplification product. In some examples, the LAMP primers amplify an HIV-1 RT nucleic acid having at least 80% sequence identify (such as at least 85%, 90%, 95%, 98%, or more sequence identity) to nucleotides 2900-3118 of the HXB2 reference sequence (e.g. GenBank Accession No. AF033819, incorporated herein by reference as present in GenBank on Nov. 6, 2014), or a portion thereof.

In some examples, the methods further include reverse transcription of HIV-1 RNA in the sample, for example by contacting the sample with a reverse transcriptase. Contacting the sample with reverse transcriptase may be prior to contacting the sample with the one or more sets of LAMP primers, or may be simultaneous with contacting the sample with the one or more sets of LAMP primers (for example in the same reaction mix with the LAMP primers). The amplification product is detected by any suitable method, such as detection of turbidity, fluorescence, or by gel electrophoresis.

LAMP primers include oligonucleotides between 15 and 60 nucleotides in length. In some embodiments, the set of LAMP primers specifically amplifies an HIV-1 INT nucleic acid. An exemplary set of LAMP primers for amplification of an HIV-1 INT nucleic acid includes an F3 primer including a nucleic acid with at least 90% sequence identity to SEQ ID NO: 8, a B3 primer including a nucleic acid with at least 90% sequence identity to SEQ ID NO: 9, an FIP primer including a nucleic acid with at least 90% sequence identity to SEQ ID NO: 10, and a BIP primer including a nucleic acid with at least 90% sequence identity to SEQ ID NO: 11, and optionally including a Loop F primer including a nucleic acid with at least 90% sequence identity to SEQ ID NO: 12, and a Loop B primer including a nucleic acid with at least 90% sequence identity to SEQ ID NO: 13, or the reverse complement of any of SEQ ID NOs: 8-13. In one example, the set of LAMP primers for HIV-1 INT nucleic acid amplification includes primers comprising, consisting essentially of, or consisting of the nucleic acid sequence each of SEQ ID NOs: 8-11. In another example, the set of LAMP primers for HIV-1 INT nucleic acid amplification includes primers comprising, consisting essentially of, or consisting of the nucleic acid sequence each of SEQ ID NOs: 8-13. In some examples, the set of LAMP primers further includes a quencher primer including a nucleic acid with at least 90% sequence identity to SEQ ID NO: 14 or the reverse complement thereof (for example, a quencher primer comprising, consisting essentially of, or consisting of the nucleic acid sequence of SEQ ID NO: 14).

In another example, a set of LAMP primers for amplification of an HIV-1 INT nucleic acid includes more than one F3 primer, more than one B3 primer, more than one FIP primer, more than one BIP primer, more than one Loop F primer, and/or more than one Loop B primer. For example, a set of LAMP primers may include one or more F3 primers, one or more B3 primers, one or more HP primers, one or more BIP primers, one or more Loop F primers and/or one or more Loop B primers. Thus, the set of LAMP primers in some examples includes primers having at least 90% identity to any combination of SEQ ID NOs: 8-13 and 15-22 or the reverse complement of any of SEQ ID NOs: 8-13 and 15-22, so long as the set of primers includes at least one each of an F3 primer, a B3 primer, an HP primer, a BIP primer, a Loop F primer, and a Loop B primer. In a specific example, a set of LAMP primers includes primers comprising, consisting essentially or, or consisting of the nucleic acid sequence of each of SEQ ID NOs: 8-13 and 15-22. In some examples, the set of LAMP primers further includes one or more quencher primers, such as one or more quencher primers having a nucleic acid sequence at least 90% identical to any one of SEQ ID NOs: 14 and 23-27 of the reverse complement thereof, for example one or more quencher primers comprising, consisting essentially of, or consisting of the nucleic acid sequence of any one of SEQ ID NOs: 14 and 23-27.

In some examples, including one or more primers for a particular LAMP primer type in the disclosed methods increases sensitivity and/or specificity of the RT-LAMP assay for detecting multiple Group M HIV-1 subtypes using a single assay. Thus, in one non-limiting example, the set of LAMP primers includes primers at least 90% identical to or comprising, consisting essentially of, or consisting of the nucleic acid sequence of each of SEQ ID NOs: 8-27. In another non-limiting example, the set of LAMP primers includes primers at least 90% identical to or comprising, consisting essentially of, or consisting of the nucleic acid sequence of each of SEQ ID NO: 8, SEQ ID NO 9, SEQ ID NO: 15, SEQ ID NO: 16, SEQ ID NO: 17, SEQ ID NO: 18, SEQ ID NO: 19, SEQ ID NO: 12, SEQ ID NO: 20, SEQ ID NO: 13, SEQ ID NO: 21, SEQ ID NO: 22, SEQ ID NO: 14 (SEQ ID NO: 23), and SEQ ID NO: 25. In some examples a primer at least 90% identical to, or comprising, consisting essentially of, or consisting of SEQ ID NO: 27 is also added to the set of LAMP primers.

In other embodiments, the set of LAMP primers specifically amplifies an HIV-1 RT nucleic acid. An exemplary set of LAMP primers for amplification of an HIV-1 RT nucleic acid includes an F3 primer including a nucleic acid with at least 90% sequence identity to SEQ ID NO: 1, a B3 primer including a nucleic acid with at least 90% sequence identity to SEQ ID NO: 2, a FIP primer including a nucleic acid with at least 90% sequence identity to SEQ ID NO: 3, and a BIP primer including a nucleic acid with at least 90% sequence identity to SEQ ID NO: 4, and optionally including a Loop F primer including a nucleic acid with at least 90% sequence identity to SEQ ID NO: 5, and a Loop B primer including a nucleic acid with at least 90% sequence identity to SEQ ID NO: 6, or the reverse complement of any of SEQ ID NOs:

1-6. In one example, the set of LAMP primers for HIV-1 RT includes primers comprising, consisting essentially of, or consisting of the nucleic acid sequence of each of SEQ ID NOs: 1-4. In another example, the set of LAMP primers for HIV-1 RT includes primers comprising, consisting essentially of, or consisting of the nucleic acid sequence of each of SEQ ID NOs: 1-6. In some examples, the set of LAMP primers additionally includes a quencher primer including a nucleic acid with at least 90% sequence identity to SEQ ID NO: 7 or the reverse complement thereof (for example, a quencher primer comprising, consisting essentially of, or consisting of the nucleic acid sequence of SEQ ID NO: 7).

The LAMP and RT-LAMP methods disclosed herein can be used with a single set of LAMP primers (such as a set of LAMP primers for HIV-1 INT nucleic acids or HIV-1 RT nucleic acid, for example, those described above). In other examples, the methods include multiplex LAMP or RT-LAMP reactions, which include two or more sets of LAMP primers for amplification of different HIV-1 target nucleic acids (such as INT and RT nucleic acids). In a particular example, a multiplex LAMP or RT-LAMP reaction includes a set of HIV-1 INT LAMP primers (such as SEQ ID NOs: 8-13, SEQ ID NOs: 8-13 and 15-22, or SEQ ID NOs: 8, 9, 12, 13, and 15-22) and a set of HIV-1 RT LAMP primers (such as SEQ ID NOs: 1-7), and optionally including one or more quencher primers (such as one or more of SEQ ID NOs: 6, 14, and 23-27). In some examples, the amount of each primer in the multiplex reaction is decreased by half compared to the amount used in a singleplex reaction (for example, the total primer concentration in the reaction remains the same). The detection method (such as a detectable label) for the INT and RT assays may be different (for example, to permit discrimination of the signal from each) or may be the same (for example, total signal is measured to determine if a sample is positive or negative for HIV-1 nucleic acids).

In other examples, a multiplex LAMP or RT-LAMP reaction includes at least one set of HIV-1 LAMP primers disclosed herein (such as SEQ ID NOs: 8-14, SEQ ID NOs: 8-27, SEQ ID NOs: 8, 9, 12-22, 25, and 27, and/or SEQ ID NOs: 1-7) and at least one set of additional HIV-2 or HIV-1 LAMP primers (such as those described in Curtis et al., *PLoS One* 7:e31432, 2012; Curtis et al., *J. Med. Virol.* 81:966-972, 2009; Curtis et al., *J. Clin. Microbiol.* 52:2674-2676, 2014; and U.S. Pat. Publ. No. 2012/0088244, all of which are incorporated by reference herein in their entirety).

The sample and LAMP primer set(s) are contacted under conditions sufficient for amplification of an HIV-1 nucleic acid (such as an HIV-1 INT nucleic acid or an HIV-1 RT nucleic acid). The sample is contacted with the set(s) of LAMP primers at a concentration sufficient to support amplification of an HIV-1 nucleic acid. In some examples, the amount of each primer is about 0.1 µM to about 5 µM (such as about 0.2 µM to about 2 µM, or about 0.5 µM to about 2 µM). Each primer can be included at a different concentration, and appropriate concentrations for each primer can be selected by one of skill in the art using routine methods. Exemplary primer concentrations are provided in Example 1, below.

In some examples, the LAMP or RT-LAMP reaction is carried out in a mixture including a suitable buffer (such as a phosphate buffer or Tris buffer). The buffer may also include additional components, such as salts (such as KCl or NaCl, magnesium salts (e.g., $MgCl_2$ or $MgSO_4$), ammonium (e.g., $(NH_4)_2SO_4$)), detergents (e.g., TRITON®-X100), or other additives (such as betaine or dimethylsulfoxide). One of ordinary skill in the art can select an appropriate buffer and any additives using routine methods. In one non-limiting example, the buffer includes 20 mM Tris-HCl, 10 mM $(NH_4)_2SO_4$, 50 mM KCl, 8 mM $MgSO_4$, 0.1% TRITON®-X100, and 0.8 M betaine. An exemplary commercially available reaction buffer is 1× Isothermal Amplification Buffer (New England Biolabs, Ipswich, Mass.). The reaction mixture also includes nucleotides or nucleotide analogs. In some examples, an equimolar mixture of dATP, dCTP, dGTP, and dTTP (referred to as dNTPs) is included, for example about 0.5-2 mM dNTPs.

A DNA polymerase with strand displacement activity is also included in the reaction mixture. Exemplary DNA polymerases include Bst DNA polymerase, Bst 2.0 DNA polymerase, Bst 2.0 WarmStart™ DNA polymerase (New England Biolabs, Ipswich, Mass.), Phi29 DNA polymerase, Bsu DNA polymerase, OmniAmp™ DNA polymerase (Lucigen, Middleton, Mich.), Taq DNA polymerase, $Vent_R$® and Deep $Vent_R$® DNA polymerases (New England Biolabs), 9° Nm™ DNA polymerase (New England Biolabs), Klenow fragment of DNA polymerase I, PhiPRD1 DNA polymerase, phage M2 DNA polymerase, T4 DNA polymerase, and T5 DNA polymerase. In some examples, about 1 to 20 U (such as about 1 to 15 U, about 2 to 12 U, about 10 to 20 U, about 2 to 10 U, or about 5 to 10 U) of DNA polymerase is included in the reaction. In some examples, the polymerase has strand displacement activity and lacks 5'-3' exonuclease activity. In one non-limiting example, the DNA polymerase is Bst 2.0 WarmStart™ DNA polymerase (New England Biolabs, Ipswich, Mass.), for example about 16 U Bst 2.0 WarmStart™ DNA polymerase per reaction.

In some embodiments, the target HIV-1 nucleic acid is RNA, and a reverse transcriptase is additionally included in the LAMP assay (called an RT-LAMP assay). Exemplary reverse transcriptases include MMLV reverse transcriptase, AMV reverse transcriptase, and ThermoScript™ reverse transcriptase (Life Technologies, Grand Island, N.Y.), Thermo-X™ reverse transcriptase (Life Technologies, Grand Island, N.Y.). In some examples, about 0.1 to 50 U (such as about 0.2 to 40 U, about 0.5 to 20 U, about 1 to 10 U, or about 2 to 5 U) of RT is included in the reaction. In a particular non-limiting example, the reaction includes 2 U/reaction of AMV RT.

The reaction mixture, including sample, LAMP primers, buffers, nucleotides, DNA polymerase, optionally reverse transcriptase, and any other components, is incubated for a period of time and at a temperature sufficient for production of an amplification product. In some examples, the reaction conditions include incubating the reaction mixture at about 37° C. to about 70° C. (such as about 40° C.–70° C., about 50° C.–65° C., or about 45° C.–60° C.), for example about 40° C., about 45° C., about 50° C., about 55° C., about 60° C., about 65° C., or about 70° C. The reaction mixture is incubated for at least about 5 minutes (such as about 10, about 15, about 20, about 30, about 40, about 50, about 60, about 70, about 80 about 90, about 100, about 110, about 120 minutes or more), for example about 10-120 minutes, about 15-90 minutes, about 20-70 minutes, about 45-75 minutes, or about 30-60 minutes. In one non-limiting example, the reaction conditions include incubating the reaction mixture at about 60° C. for about 60 minutes. The reaction can optionally be terminated by incubation for a short time at a higher temperature, for example about 2-10 minutes at about 80° C. In some examples, the assay is performed using a chemical heater device to maintain the sample at the reaction temperature for a period of time (see, e.g., Singleton et al., *Proc. SPIE* 8615:8625oR, 2013; Curtis et al., *PLoS ONE* 7:e31432, 2012).

Following incubation of the reaction mixture, the amplification product is detected by any suitable method. The detection methods may be quantitative, semi-quantitative, or qualitative. Accumulation of an amplification product (for example, compared to a negative control, such as a reagent only control) indicates presence of HIV-1 nucleic acids in the sample. In some examples, accumulation of an amplification product is detected by measuring the turbidity of the reaction mixture (for example, visually or with a turbidometer). In other examples, amplification product is detected using gel electrophoresis, for example by detecting presence or amount of amplification product with agarose gel electrophoresis. In some examples, amplification product is detected using a colorimetric assay, such as with an intercalating dye (for example, propidium iodide, SYBR green or Picogreen) or a chromogenic reagent (see, e.g., Goto et al., *BioTechniques* 46:167-172, 2009).

In further examples, amplification product is detected by a fluorescent indicator dye such as calcein (see, e.g., Tomita et al., *Nat. Protoc.* 3:877-882, 2008). In other examples, amplification products are detected using a detectable label incorporated in one or more of the LAMP primers (discussed below). The detectable label may be optically detectable, for example, by eye or using a spectrophotometer or fluorimeter. In some examples, the detectable label is a fluorophore, such as those described above. In some examples, the label is detected in real-time, for example using a fluorescence scanner (such as ESEQuant, Qiagen). One of skill in the art can select one or more detectable labels for use in the methods disclosed herein.

In particular embodiments, one of the LAMP primers includes a detectable label, such as a fluorophore. In a specific example, the Loop B primer (for example, SEQ ID NOs: 6, 13, 21, and/or 22) or the Loop F primer (for example SEQ ID NOs: 5, 12, and/or 20) includes a fluorophore, for example attached to the 5' end or the 3' end of the primer. Any fluorophore can be used; in one non-limiting example, the fluorophore is HEX. In particular non-limiting examples, the HIV-1 INT Loop B primer (e.g., SEQ ID NOs: 13, 21, and/or 22) includes a 5' fluorophore, such as HEX. In another non-limiting example, the HIV-1 RT Loop F primer (e.g., SEQ ID NO: 6) includes a 5' fluorophore, such as HEX.

In embodiments including a quencher primer, the quencher includes an acceptor fluorophore (a quencher). The quencher primer is complementary to at least a portion of the labeled primer and reduces or even substantially eliminates detectable fluorescence from the labeled primer if the labeled primer is not incorporated in the LAMP amplification product, thus reducing background or non-specific fluorescence in the reaction. In some examples, the quencher primer includes a BLACK HOLE quencher, for example, attached to the 5' end or the 3' end of the primer. Exemplary quenchers include BHQ1, BHQ2, or BHQ3. In particular non-limiting examples, the HIV-1 INT quencher primer (e.g., any one of SEQ ID NOs: 14 and 23-27) includes a 3' quencher, such as BHQ1. In another non-limiting example, the HIV-1 RT quencher primer (e.g., SEQ ID NO: 7) includes a 3' quencher, such as BHQ1.

III. Primers and Kits

Primers (such as isolated nucleic acid primers) suitable for use in the disclosed methods are described herein. In some examples, the primers are suitable for detection of HIV-1 nucleic acids using LAMP or RT-LAMP assays described herein.

In some embodiments, the disclosed primers are between 10 and 60 nucleotides in length, such as 10, 11, 12, 13, 14, 15, 16, 17, 18, 19, 20, 21, 22, 23, 24, 25, 26, 27, 28 29, 30, 31, 32, 32, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length and are capable of hybridizing to, and in some examples, amplifying the disclosed nucleic acid molecules. In some examples, the primers and/or probes are at least 10, 15, 20, 25, 30, 35, 40, 45, 50, 55, or 60 nucleotides in length. In other examples, the primers and/or probes may be no more than 10, 15, 20, 25, 30, 35, 40, 45, 50, 55, or 60 nucleotides in length.

In some examples, the disclosed primers include LAMP primers for amplification of HIV-1 INT nucleic acids, including primers including a nucleic acid sequence with at least 90% sequence identity (for example, at least 91%, 92%, 93%, 94%, 95%, 96%, 97%, 98%, 99%, or 100% identity) to SEQ ID NO: 8 (F3), SEQ ID NOs: 9 or 15 (B3), SEQ ID NOs: 10, 16, or 17 (HP), SEQ ID NOs: 11, 18, or 19 (BIP), SEQ ID NOs: 12 or 20 (Loop F), SEQ ID NOs: 13, 21, or 22 (Loop B), and/or SEQ ID NOs: 14 or 23-27 (quencher), or the reverse complement of any thereof.

In other examples, the disclosed primers include LAMP primers for amplification of HIV-1 RT nucleic acids, including primers with at least 90% sequence identity (for example, at least 91%, 92%, 93%, 94%, 95%, 96%, 97%, 98%, 99%, or 100% identity) to SEQ ID NO: 1 (F3), SEQ ID NO: 2 (B3), SEQ ID NO: 3 (FIP), SEQ ID NO: 4 (BIP), SEQ ID NO: 5 (Loop F), SEQ ID NO: 6 (Loop B), and/or SEQ ID NO: 7 (quencher) or the reverse complement of any thereof.

In some examples, at least one of the primers includes a detectable label, such as a fluorophore. In particular examples, a Loop B primer (e.g., SEQ ID NOs: 6, 13, 21, and/or 22) includes a fluorophore at the 5' or 3' end, which is HEX in one non-limiting example. In other examples, the Loop F primer (e.g., SEQ ID NOs: 5, 12, and/or 20) includes a fluorophore at the 5' or 3' end, which is HEX in one non-limiting example. In other examples, the quencher (e.g., SEQ ID NOs: 7, 14, or 23-27) includes a fluorescence quencher at the 5' or 3' end, such as a dark quencher, which is BHQ1 in one non-limiting example.

Although exemplary primer sequences are provided herein, the primer sequences can be varied slightly by moving the primer a few nucleotides upstream or downstream from the nucleotide positions that they hybridize to on the target nucleic molecule acid, provided that the probe and/or primer is still specific for the target nucleic acid sequence. For example, variations of the primers disclosed as SEQ ID NOs: 1-27 can be made by "sliding" the probes or primers a few nucleotides 5' or 3' from their positions, and such variations will still be specific for the respective target nucleic acid sequence.

Also provided by the present disclosure are primers that include variations to the nucleotide sequences shown in any of SEQ ID NOs: 1-27, as long as such variations permit detection of the target nucleic acid molecule. For example, a primer can have at least 90% sequence identity such as at least 91%, 92%, 93%, 94%, 95%, 96%, 97%, 98%, or 99% identity to a nucleic acid including the sequence shown in any of SEQ ID NOs: 1-27. In such examples, the number of nucleotides does not change, but the nucleic acid sequence shown in any of SEQ ID NOs: 1-27 can vary at a few nucleotides, such as changes at 1, 2, 3, 4, 5, or 6 nucleotides.

The present application also provides primers that are slightly longer or shorter than the nucleotide sequences shown in any of SEQ ID NOs: 1-27, as long as such deletions or additions permit amplification and/or detection of the desired target nucleic acid molecule. For example, a primer can include a few nucleotide deletions or additions at the 5'- or 3'-end of the primers shown in any of SEQ ID NOs: 1-27, such as addition or deletion of 1, 2, 3, 4, 5, or 6 nucleotides from the 5'- or 3'-end, or combinations thereof (such as a deletion from one end and an addition to the other end). In such examples, the number of nucleotides changes.

Also provided are primers that are degenerate at one or more positions (such as 1, 2, 3, 4, 5, or more positions), for example, a primer that includes a mixture of nucleotides (such as 2, 3, or 4 nucleotides) at a specified position in the primer. In other examples, the primers disclosed herein include one or more synthetic bases or alternative bases (such as inosine). In other examples, the primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). In other examples, the primers disclosed herein include a minor groove binder conjugated to the 5' or 3' end of the oligonucleotide (see, e.g., U.S. Pat. No. 6,486,308).

The nucleic acid primers disclosed herein can be supplied in the form of a kit for use in the detection or amplification of one or more HIV-1 nucleic acids. In such a kit, an appropriate amount of one or more of the nucleic acid primers (such as one or more of SEQ ID NOs: 1-27) are provided in one or more containers or in one or more individual wells or channels of a multiwell plate or card or a microfluidic device. A nucleic acid primer(s) may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid primers (for example, 1, 2, 3, 4, 5, 6, 7, 8, 9, 10, 11, 12, 13, 14, 15, 16, 17, 18, 19, 20, 21, 22, 23, 24, 25, 26, 27, or more primers) for use in amplification and/or detection of HIV-1 nucleic acids. One or more positive and/or negative control primers and/or nucleic acids also may be supplied in the kit. Exemplary negative controls include non-HIV-1 nucleic acids (such as HIV-2 or HTLV nucleic acids) or non-viral nucleic acids (such as human nucleic acids). Exemplary positive controls include primers and nucleic acids for amplification of human target nucleic acids (such as human (3-actin or RNaseP) or primers and nucleic acids for other HIV-1 target nucleic acids (for example other regions of the INT gene or other HIV-1 genes). One of ordinary skill in the art can select suitable positive and negative controls for the assays disclosed herein.

In some examples, one or more primers (such as one or more sets of primers), are provided in pre-measured single use amounts in individual, typically disposable, tubes, wells, microfluidic devices, or equivalent containers. In this example, the sample to be tested for the presence of the target nucleic acids can be added to the individual tube(s) or well(s) and amplification and/or detection can be carried out directly. The kit may also include additional reagents for the detection and/or amplification of HIV-1 nucleic acids, such as buffer(s), nucleotides (such as dNTPs), enzymes (such as DNA polymerase and/or reverse transcriptase), or other suitable reagents. The additional reagents may be in separate container(s) from the one or more primers or may be included in the same container as the primer(s).

In particular examples, the kits include at least one set of LAMP primers for amplification and/or detection of HIV-1 nucleic acids. In one example, the kit includes a set of primers including SEQ ID NOs: 8-13, and optionally SEQ ID NO: 14. In another example, the kit includes a set of primers including SEQ ID NOs: 1-6, and optionally SEQ ID NO: 7. In yet another example, the kit includes two sets of LAMP primers, including SEQ ID NOs: 8-13 and SEQ ID NOs: 1-6, the kit optionally also including SEQ ID NOs: 14 and 7. In another example, the kit includes a set of LAMP primers including SEQ ID NOs: 8-13 and 15-22; optionally the kit also includes primers including SEQ ID NOs: 14 and 23-27. In a further example, the kit includes two sets of LAMP primers, including SEQ ID NOs: 1-6, 8-13, and 15-22; optionally further including primers including SEQ ID NOs: 7, 14, and 23-27.

In another example, the kit includes a set of LAMP primers including SEQ ID NO: 8, SEQ ID NO: 9, SEQ ID NO: 15, SEQ ID NO: 16, SEQ ID NO: 17, SEQ ID NO: 18, SEQ ID NO: 19, SEQ ID NO: 12, SEQ ID NO: 20, SEQ ID NO: 13, SEQ ID NO: 21, SEQ ID NO: 22, and optionally, at least one (such as 1, 2, or all) of SEQ ID NO: 14 (SEQ ID NO: 23), SEQ ID NO: 25, and SEQ ID NO: 27. The kit may further include a second set of LAMP primers including SEQ ID NOs: 1-6 and optionally SEQ ID NO: 7.

The present disclosure is illustrated by the following non-limiting Examples.

Example 1

RT-LAMP Assay for Detection of HIV-1

This example describes detection of HIV-1 nucleic acids using an RT-LAMP assay.

Materials and Methods

RT-LAMP Primers and Quenchers:

HIV-1 RT-LAMP primers specific for the RT gene region have previously been described (Curtis et al., *PLoS ONE* 7:e31432, 2012, shown in Table 1). In the present study, a truncated version of the RT quencher probe with a 3' BHQ-1 label (SEQ ID NO: 7; Table 1) was designed to be added directly into the reaction mix as opposed to adding post-reaction, as in previous studies. This eliminates the need to open the reaction tubes after amplification and reduces the risk of amplicons being released and contaminating the work environment. An additional HIV-1 primer set was designed in a highly conserved region of the INT gene, using PrimerExplorer V3 software available on the Eiken Chemical Co. Ltd. (Japan) website (available on the World Wide Web at primerexplorer.jp/e/). The HIV-1 HXB2 sequence (GenBank Accession No. AF033819) was used as the reference for generating the primers. The primers generated using PrimerExplorer were then individually aligned with multiple subtype sequences using the Los Alamos HIV sequence database (available on the World Wide Web at hiv.lanl.gov). A consensus sequence was generated for each subtype based on the percent occurrence of each base pair within the isolate sequences that are listed in the database. Candidate primers were then screened with diverse isolates and sequences altered to account for mismatches that only become apparent upon empirical testing. The sequences of the selected INT primers and quencher probe (and RT primers and quencher) are listed in Table 1.

TABLE 1

HIV-1 RT-LAMP primer sequences

| Gene | Primer Name | HBX2 Location | Primer Sequence (5'-3') | SEQ ID NO: |
|---|---|---|---|---|
| RT | F3 | 2900-2920 | AGTTCCCTTAGATAAAGACTT | 1 |
|  | B3 | 3097-3118 | CCTACATACAAATCATCCATGT | 2 |
|  | FIP | 2976-3000, 2919-2944 | GTGGAAGCACATTGTACTGATATCTTT TTGGAAGTATACTGCATTTACCAT | 3 |
|  | BIP | 3007-3031, 3056-3078 | GGAAAGGATCACCAGCAATATTCCTCT GGATTTTGTTTTCTAAAAGGC | 4 |
|  | Loop F | 2948-2968 | HEX-GGTGTCTCATTGTTTATACTA | 5 |
|  | Loop B | 3037-3055 | GCATGACAAAAATCTTAGA | 6 |
|  | Quencher | 2954-2968 | AAACAATGAGACACC-BHQ1 | 7 |
| INT | F3 | 4901-4920 | GGTTTATTACAGGGACAGCA | 8 |
|  | B3 | 5070-5087 | ATCCTGTCTACTTGCCAC | 9 |
|  | FIP | 4963-4986, 4923-4942 | CTTGTATTACTACTGCCCCTTCA CGATCCACTTTGGAAAGGACC | 10 |
|  | BIP | 4994-5018, 5051-5069 | TGACATAAAAGTAGTGCCAAGAAGATT TTACAATCATCACCTGCCATC | 11 |
|  | Loop F | 4943-4962 | CTTTCCAGAGAAGCTTTGCT | 12 |
|  | Loop B | 5021-5042 | HEX-AGCAAAGATCATTAGGGA TTAT | 13 |
|  | Quencher | 5021-5034 | TAATGATCTTTGCT-BHQ1 | 14 |
|  | B3-2 | 5070-5087 | ATCCTGTCTACCTGCCAC | 15 |
|  | FIP-1 | 4963-4986, 4923-4942 | CTTGTATTACTACTGCCCCTTCACGAYC CAATTTGGAAAGGACC | 16 |
|  | FIP-2 | 4963-4986, 4923-4942 | CTTGTATTACTACTGCCCCTTCACGACC CTATTTGGAAAGGACC | 17 |
|  | BIP-1 | 4994-5018, 5051-5069 | TGATATAAARGTAGTACCAAGAAGATT TTACAATCATCACCTGCCATC | 18 |
|  | BIP-2 | 4994-5018, 5051-5069 | TGACATAAAGGTAGTACCAAGGAGGTT TTACAATCAGCACCTGCCATC | 19 |
|  | Loop F-2 | 4943-4962 | CTTTCCAGAGTAGTTTTGCT | 20 |
|  | Loop B-2 | 5021-5042 | HEX-AGTAAAAATCATTAAGGACTAT | 21 |
|  | Loop B-3 | 5021-5042 | HEX-AGCAAAAATCATTAAGGATTAT | 22 |
|  | Truncated Quencher 1 | 5021-5034 | TAATGATCTTTGCT-BHQ1 | 23 |
|  | Full-length Quencher 2 | 5016-5037 | ATAGTCCTTAATGATTTTTACT-BHQ1 | 24 |
|  | Truncated Quencher 2 | 5021-5037 | CCTTAATGATTTTTACT-BHQ1 | 25 |
|  | Full-length Quencher 3 | 5016-5037 | ATAATCCTTAATGATTTTTGCT-BHQ1 | 26 |
|  | Truncated Quencher 3 | 5021-5037 | CCTTAATGATTTTTGCT-BHQ1 | 27 |

HIV-1 DNA and RNA Linearity Panels:

An HIV-1 DNA linearity panel was created using the human monocytic cell line OM-10.1, which contains a single integrated HIV-1 provirus per cell (Butera et al., *J. Virol.* 65:4645-4553, 1991). DNA was extracted using a QIAamp DNA Blood Mini kit (Qiagen, Valencia, Calif.), as previously described (Curtis et al., *J. Med. Virol.* 81:966-972, 2009). A panel was created ranging from $10^5$ to $10^2$ copies/ml using serial, tenfold dilutions in DEPC-treated water (Invitrogen, Carlsbad, Calif.). A negative DNA control was generated by extracting DNA from peripheral blood mononuclear cells (PBMCs) infected with an HIV-2 isolate, NIH-Z (Advanced Biotechnologies, Inc., Columbia, Md.). Due to the genetic diversity between HIV-1 and HIV-2 and the specificity of the RT-LAMP assay, HIV-1 primers should not amplify HIV-2 targets.

An HIV-1 RNA linearity panel was also created using the supernatant from 8E5 cells (ATCC, Manassas, Va.), which contain a single defective proviral genome of HIV-1 per cell, but still express virus in the supernatant. The viral load of the cell supernatant was determined using the Roche COBAS® AmpliPrep/COBAS® TaqMan HIV-1 Test V2.0 (Roche Diagnostics, Indianapolis, Ind.) and the supernatant was spiked into uninfected human plasma. Serial dilutions were made in plasma to create a panel that ranged from $10^6$ to $10^3$ RNA copies/ml. RNA was extracted from the panel using a QIAamp Viral RNA Mini Kit (QIAGEN, Valencia, Calif.). Positive and negative controls included RNA extracted from HIV-1 BaL purified virus and HIV-2 NIH-Z purified virus (Advanced Biotechnologies Inc., Columbia, Md.), respectively. Aliquots of both linearity panels were made and stored at −80° C. until use.

HIV-1 Seroconversion Panels:

Serial plasma specimens were collected from 12 U.S. donors that became HIV-1 infected during the collection period. The seroconversion panels were obtained from SeraCare Life Sciences (n=7) (Gaithersburg, Md.) and ZeptoMetrix Corp. (n=5) (Buffalo, N.Y.). All of the samples in these panels were obtained from individuals with HIV-1 subtype B infection.

The Multispot HIV-1/HIV-2 Rapid Test (Bio-Rad, Redmond, Calif., also referred to herein as "rapid Ab"), GS HIV-1 Western blot (Bio-Rad, also referred to herein as "WB"), third-generation GS HIV-1/HIV-2 Plus 0 EIA (Bio-Rad, also referred to herein as "Ab EIA"), fourth-generation GS HIV Combo Ag/Ab EIA (Bio-Rad, also referred to herein as "Ab+Ag EIA"), and APTIMA HIV-1 Qualitative Assay (Hologic Inc., San Diego, Calif., also referred to herein as "RNA") test results were considered for comparison with the RT-LAMP assay. For the SeraCare panels, all HIV test results were supplied by the manufacturer, with the exception of the Multispot and the APTIMA, which were performed in-house according to the package inserts. Viral loads were determined using the COBAS® AmpliPrep/COBAS® TaqMan HIV-1 Test V2.0 (Roche Diagnostics, Indianapolis, Ind.), except for panels PRB970 and PRB946 which were determined by the COBAS® AmpliPrep/COBAS® TaqMan HIV-1 Test V1.0 (Roche Diagnostics, Indianapolis, Ind.) and the Amplicor HIV-1 Monitor Test (Roche Diagnostics, Indianapolis, Ind.), respectively. For the ZeptoMetrix panels, all HIV testing was performed in-house according to the package inserts. The viral loads for each sample were determined by the COBAS® AmpliPrep/COBAS® TaqMan HIV-1 Test V2.0. For RT-LAMP testing, RNA was extracted from the panels using a QIAamp Viral RNA Mini Kit.

RT-LAMP Reaction.

The RT-LAMP reaction was performed as described previously (Curtis et al., *J. Med. Virol.* 81:966-972, 2009), with a few modifications. Briefly, the RT-LAMP reaction mix (25 µl volume total) contained a final concentration of 0.2 µM each of F3 and B3 primers, 1.6 µM each of HP and BIP primers, 0.8 µM each of LoopF and LoopB primers (a 5' HEX label is added to LoopF for RT and to LoopB for INT), 0.8 M Betaine (Sigma-Aldrich, St. Louis, Mo.), 8 mM MgSO$_4$, 1.4 mM dNTPs (Roche Applied Science, Indianapolis, Ind.), 1× Isothermal Amplification Buffer (New England Biolabs, Ipswich, Mass.), 16U Bst 2.0 WarmStart DNA Polymerase (New England Biolabs) and 2U AMV Reverse Transcriptase (Life Technologies, Carlsbad, Calif.). The addition of a reverse transcriptase enzyme allowed the amplification of both DNA and RNA simultaneously in the same reaction tube. In addition, a 3' BHQ1-labeled quencher probe was added into the reaction at a final concentration of 0.8 µM. To the reaction mixture, 10 µl of extracted DNA or RNA was added. The reaction mixture was heated at 60° C. for 60 minutes, using a GeneAmp® PCR System 9700 (Applied Biosystems, Foster City, Calif.), then held at 80° C. for 2 minutes to terminate the reaction. In addition to positive and negative controls, a reagent (no template) control was included in every run to check for reagent contamination. The presence of amplified product was determined visually by observing fluorescence in the reaction tubes using the UV lamp from a GelDoc™ XR+Imaging System (BioRad Laboratories, Hercules, Calif.).

Results

Figure 1B:
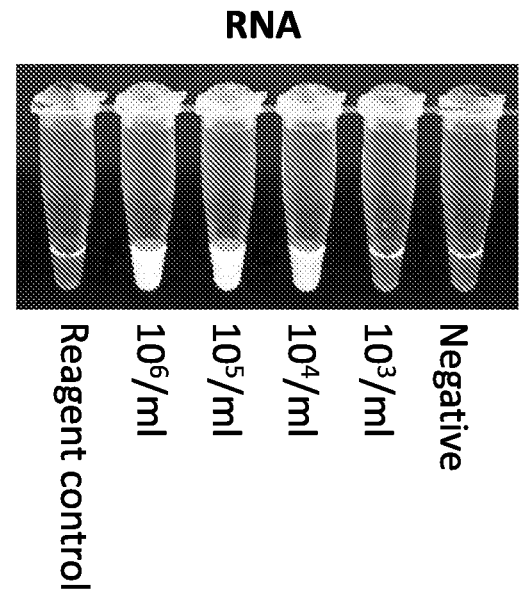

HIV-1 INT RT-LAMP Sensitivity:

The sensitivity of the HIV-1 RT-LAMP assay using the RT primers has been previously described (Curtis et al., *PLoS ONE* 7:e31432. 2-12). The sensitivity of the assay for both DNA and RNA using the INT primers was similar to the reported sensitivity for the RT primers. A representative experiment demonstrating amplification of HIV-1 DNA and RNA linearity panels is shown in FIGS. 1A and 1B, respectively. The limit of detection was $10^2$ DNA copies/ml and $10^5$ to $10^4$ RNA copies/ml, depending on the experiment. No amplification was observed in the negative control or the reagent control tube.

Evaluation of RT-LAMP Assay with Acute HIV-1 Clinical Samples:

To determine the ability of the RT-LAMP assay (SEQ ID NOs: 8-14) to detect samples from acute HIV-1 infection, seroconversion panels were tested. For the SeraCare samples (n=7), only one of the panels became reactive during the sample collection period by the rapid Ab test. This particular sample became rapid Ab reactive 14 days after the first detectable viral load. In contrast, all of the SeraCare panels were reactive by the HIV-1 RT-LAMP assay between 0 and 2 days after the first detectable viral load (Table 2). For most panels, both the RT and INT primers detected samples from the same time point; however, in select cases, one primer set detected a sample prior to the other. In comparison to the laboratory-based tests, the RT-LAMP assay detected members in all seroconversion panels prior to the Ab EIA, and 0 to 7 days prior to the Ab+Ag EIA. The RT-LAMP assay detected panel members a minimum of 3 to 15 days prior to WB. In comparison to the qualitative RNA data, the RT-LAMP assay became positive at the same time point or up to 2 days later than the APTIMA assay. Based on the viral load data from the panel, both the RT and INT primer sets detected all of the samples in the expected sensitivity range of the assay (Table 2).

TABLE 2

Evaluation of RT-LAMP assay with SeraCare seroconversion panels

| Panel ID | Days Since 1$^{st}$ VL* | Viral Load | WB | Ab EIA | Ab + Ag EIA | Rapid Ab | RNA | RT RT-LAMP | INT RT-LAMP |
|---|---|---|---|---|---|---|---|---|---|
| PRB973-01 | 0 | 1.8 × 10$^3$ | − | − | − | − | + | − | − |
| PRB973-02 | 2 | 1.7 × 10$^4$ | − | − | − | − | + | + | + |
| PRB973-03 | 7 | 1.7 × 10$^5$ | − | − | + | − | + | + | + |
| PRB973-04 | 11 | 1.5 × 10$^6$ | IND | + | + | − | + | + | + |
| PRB974-01 | −7 | BLD | − | − | − | − | − | − | − |
| PRB974-02 | 0 | 8.6 × 10$^3$ | − | − | − | − | + | + | + |
| PRB974-03 | 2 | 8.3 × 10$^4$ | − | − | + | − | + | + | + |
| PRB974-04 | 9 | 9.6 × 10$^5$ | − | − | + | − | + | + | + |
| PRB975-01 | −7 | BLD | − | − | − | − | − | − | − |
| PRB975-02 | −5 | BLD | − | − | − | − | − | − | − |
| PRB975-03 | 0 | 1.4 × 10$^2$ | − | − | − | − | + | − | − |
| PRB975-04 | 2 | 2.1 × 10$^3$ | − | − | − | − | + | + | + |
| PRB975-05 | 7 | 1.8 × 10$^6$ | − | − | + | − | + | + | + |
| PRB976-01 | 0 | 1.2 × 10$^4$ | − | − | − | − | + | +/− | + |
| PRB976-02 | 2 | 2.1 × 10$^4$ | − | − | − | − | + | + | + |
| PRB976-03 | 7 | 6.3 × 10$^5$ | − | − | + | − | + | + | + |
| PRB976-04 | 9 | 1.9 × 10$^6$ | − | − | + | − | + | + | + |
| PRB977-01 | 0 | 1.9 × 10$^2$ | − | − | − | − | + | − | − |
| PRB977-02 | 2 | 3.5 × 10$^3$ | − | − | − | − | + | − | +/− |
| PRB977-03 | 13 | 1.6 × 10$^6$ | − | − | + | − | + | + | + |
| PRB977-04 | 15 | 1.0 × 10$^7$ | − | + | + | − | + | + | + |

TABLE 2-continued

Evaluation of RT-LAMP assay with SeraCare seroconversion panels

| Panel ID | Days Since 1st VL* | Viral Load | WB | Ab EIA | Ab + Ag EIA | Rapid Ab | RNA | RT RT-LAMP | INT RT-LAMP |
|---|---|---|---|---|---|---|---|---|---|
| PRB970-01 | 0 | $1.6 \times 10^5$ | − | − | + | − | + | + | + |
| PRB970-02 | 7 | $>1 \times 10^7$ | − | − | + | − | + | + | + |
| PRB970-03 | 10 | $2.8 \times 10^6$ | − | + | + | − | + | + | + |
| PRB970-04 | 14 | $6.5 \times 10^4$ | IND | + | + | + | + | + | + |
| PRB946-01 | −4 | BLD | − | − | ND | − | − | − | − |
| PRB946-02 | 0 | $3.0 \times 10^4$ | − | − | ND | − | + | +/− | − |
| PRB946-03 | 3 | $7.0 \times 10^5$ | − | − | ND | − | + | + | + |
| PRB946-04 | 7 | $>8 \times 10^5$ | − | − | ND | − | + | + | + |

+, reactive test result;
−, non-reactive test result;
+/−, reactive in 1 of 2 replicates;
IND, indeterminate;
ND, no data;
*first detectable viral load For the ZeptoMetrix panels (n=5), the rapid Ab test detected panel members 7 to 29 days post first detectable viral load. In contrast, the RT-LAMP assay (SEQ ID NOs: 8-14) detected panel members within 0 to 5 days post first detectable viral load, which was 7 to 24 days earlier than the rapid Ab test. Overall, comparable reactivity was observed between the RT and the INT primers for RT-LAMP with this panel (Table 3). In comparison to the laboratory-based tests, the RT-LAMP assay detected panel members anywhere from 2 to 14 days prior to the Ab EIA and 0 to 14 days prior to the Ab+Ag EIA. The RT-LAMP assay was able to detect samples 9 to 29 days before the WB assay. In comparison to the qualitative RNA data, the RT-LAMP assay became positive at the same time point or up to 5 days later than the APTIMA assay. Overall, the RT-LAMP assay detected the majority of panel members within the expected viral load sensitivity range (Table 3).

TABLE 3

Evaluation of RT-LAMP assay with ZeptoMetrix seroconversion panels

| Panel ID | Days Since 1st VL* | Viral Load | WB | Ab EIA | Ab + Ag EIA | Rapid Ab | RNA | RT RT-LAMP | INT RT-LAMP |
|---|---|---|---|---|---|---|---|---|---|
| 6240-6 | 0 | $2.43 \times 10^1$ | − | − | − | − | + | − | − |
| 6240-7 | 5 | $2.41 \times 10^4$ | − | − | − | − | + | + | + |
| 6240-8 | 7 | $8.42 \times 10^4$ | IND | − | + | − | + | + | + |
| 6240-9 | 12 | $7.28 \times 10^5$ | IND | − | + | − | + | + | + |
| 6240-10 | 14 | $1.45 \times 10^6$ | IND | + | + | − | + | + | + |
| 6240-12 | 29 | $5.07 \times 10^4$ | + | + | + | + | + | + | + |
| 12007-3 | −63 | BLD | − | − | − | − | − | − | − |
| 12007-4 | 0 | $1.80 \times 10^5$ | − | − | + | − | + | + | + |
| 12007-5 | 2 | $1.29 \times 10^5$ | IND | + | + | − | + | + | + |
| 12007-6 | 7 | $4.89 \times 10^4$ | IND | + | + | + | + | + | + |
| 12007-7 | 9 | $4.91 \times 10^4$ | + | + | + | − | + | + | + |
| 12008-6 | −5 | BLD | ND | − | − | − | − | − | − |
| 12008-7 | 0 | $9.99 \times 10^2$ | ND | − | − | − | + | +/− | − |
| 12008-8 | 2 | $3.20 \times 10^4$ | − | − | − | − | + | + | + |
| 12008-9 | 7 | $4.70 \times 10^6$ | − | − | + | − | + | + | + |
| 12008-10 | 12 | $>1.0 \times 10^7$ | − | + | + | − | + | + | + |
| 12008-11 | 14 | $>1.0 \times 10^7$ | + | + | + | − | + | + | + |
| 12008-12 | 19 | $1.09 \times 10^5$ | + | + | + | + | + | + | + |
| 9079-8 | 0 | $2.08 \times 10^1$ | ND | − | − | − | + | − | − |
| 9079-9 | 5 | $9.60 \times 10^4$ | − | − | + | − | + | + | + |
| 9079-10 | 7 | $3.40 \times 10^5$ | − | − | + | − | + | + | + |
| 9079-11 | 12 | $8.32 \times 10^5$ | − | + | + | − | + | + | + |
| 9079-12 | 14 | $1.33 \times 10^6$ | IND | + | + | − | + | + | + |
| 9079-13 | 20 | $1.56 \times 10^5$ | IND | + | + | + | + | + | + |
| 9079-14 | 22 | $3.0 \times 10^4$ | IND | + | + | + | + | + | +/− |
| 9079-15 | 27 | $7.21 \times 10^3$ | + | + | + | + | + | + | − |
| 9032-6 | 0 | $1.62 \times 10^3$ | − | − | − | − | + | − | − |
| 9032-7 | 5 | $4.49 \times 10^4$ | − | − | − | − | + | + | + |
| 9032-8 | 7 | $2.76 \times 10^4$ | − | − | − | − | + | + | +/− |
| 9032-9 | 12 | $2.81 \times 10^4$ | IND | − | − | − | + | + | + |
| 9032-10 | 19 | $3.72 \times 10^3$ | IND | + | + | + | + | + | + |

TABLE 3-continued

Evaluation of RT-LAMP assay with ZeptoMetrix seroconversion panels

| Panel ID | Days Since 1st VL* | Viral Load | WB | Ab EIA | Ab + Ag EIA | Rapid Ab | RNA | RT RT-LAMP | INT RT-LAMP |
|---|---|---|---|---|---|---|---|---|---|
| 9032-11 | 21 | $3.42 \times 10^3$ | IND | + | + | + | + | + | + |
| 9032-12 | 32 | $5.94 \times 10^3$ | IND | + | + | + | + | + | − |
| 9032-13 | 34 | $1.03 \times 10^3$ | + | + | + | + | + | +/− | − |

Figure 2:
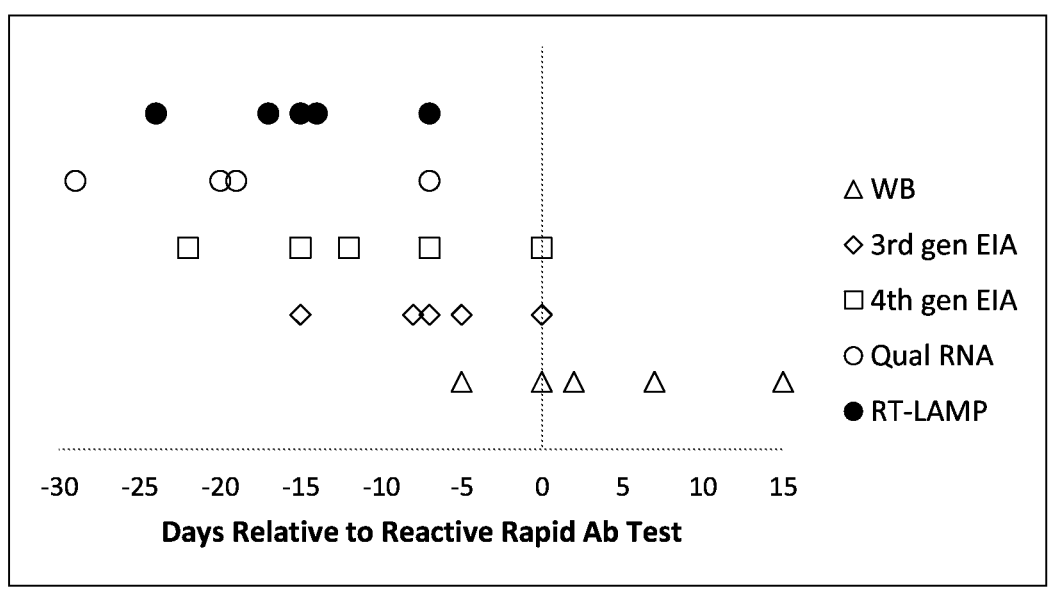
FIG. 2 is a graph showing the timing of test positivity in relation to the rapid antibody test (Day 0) for the ZeptoMetrix cohort. Each data point represents an individual test result. WB, GS HIV-1 Western blot; $3^{rd}$ gen enzyme immunoassay (EIA), GS HIV-1/HIV-2 Plus 0 EIA; $4^{th}$ gen EIA, GS HIV Combo Ag/Ab EIA, Qual RNA, APTIMA HIV-1 qualitative RNA assay; RT-LAMP, HIV-1 INT RT-LAMP assay.

+, reactive test result;
−, non-reactive test result;
+/−, reactive in 1 of 2 replicates;
IND, indeterminate;
ND, no data;
*first detectable viral load A summary of the HIV-1 test results for these panels, in relation to the first rapid Ab reactive test result is shown in FIG. 2. The SeraCare panels were not included in the timeline because of the short follow-up time and the fact that only one subject became rapid Ab test reactive during the sample collection period.

In addition, INT RT-LAMP primers (SEQ ID NOs: 8, 9, 12-23, 25, and 27) were evaluated using RNA linearity panels generated from an international panel of subtype isolates. The isolate panel was obtained from the NIH AIDS Reagent Program (www.aidsreagentorg/reagentdetail.cfm?t=viruses&id=671). Each member of the panel is cell-free, virus supernatant. The virus was quantified and dilutions made to produce the appropriate panel members. Each sample was tested in duplicate. The majority of the isolates were detected at $10^4$-$10^5$ RNA copies/ml (Table 4).

TABLE 4

Performance of HIV-1 INT RT-LAMP primers with group M isolates

| Isolate | Subtype | RNA copies/ml |||||||||
|---|---|---|---|---|---|---|---|---|---|---|
| | | $10^7$ | | | $10^6$ | | $10^5$ | $10^4$ | | $10^3$ |
| 92UG029 | A | + | + | + | + | + | + | + | − | − | − |
| 93RW024 | A | + | + | + | + | + | + | − | − | − | − |
| KER2008 | A | + | + | + | + | + | + | + | + | − | − |
| KER2018 | A | + | + | + | + | + | + | − | − | − | − |
| 90SE364 | C | + | + | + | + | + | + | + | + | + | − |
| 89SM145 | C | + | + | + | + | + | + | + | + | − | − |
| PBL288 | C | + | + | + | + | + | − | − | − | − | − |
| TZDB9/11 | C | + | + | + | + | + | + | + | + | − | − |
| 99UGA03349M1 | D | + | + | + | + | + | − | − | − | − | − |
| 99UGA07412M1 | D | + | + | + | + | + | + | + | − | − | − |
| 98UG57128 | D | + | + | + | + | + | − | + | − | − | − |
| 93UG065 | D | + | + | + | + | + | + | + | + | − | − |
| 90THCM240 | AE | + | + | + | + | + | + | + | + | − | − |
| 90THCM244 | AE | + | + | + | + | + | + | + | − | − | − |
| 90THCM235 | AE | + | + | + | + | + | + | + | − | − | − |
| 96THM02138 | AE | + | + | + | + | + | + | + | + | − | − |
| CAM0005BBY | AG | + | + | + | + | + | + | − | − | − | − |
| CAM0014BBY | AG | + | + | + | + | + | + | + | + | − | − |
| CAM0002BBY | AG | + | + | + | + | + | + | − | − | − | − |
| 98USMSC5007 | AG | + | + | + | + | + | + | − | − | − | − |

+, reactive test result;
−, non-reactive test result

Discussion

In the studies described above, the primary focus was RNA detection, since high plasma viral loads are characteristic of acute infection; however, proviral DNA may also be detected in whole blood. To enable immediate naked eye visualization of the amplified products, a sequence-specific fluorescent detection method was developed for the HIV-1 RT-LAMP assay (Curtis et al., J. Med. Virol. 81:966-972, 2009). The previously described assay was further modified by adding the quencher probe directly into the reaction, which eliminated the need to open the reaction tubes post-amplification. A large amount of amplicons are produced during the LAMP process and reducing the risk of releasing these amplicons into the testing environment is crucial for non-laboratory settings. For POC use, it is advantageous to be able to assess sample positivity immediately post-amplification, without any additional steps.

Further assay improvements included the design of a novel primer set that recognized a conserved region within the HIV-1 integrase (INT) sequence. Although assay performance for the RT and INT primer sets was demonstrated separately for comparison purposes, the primer sets can be combined in a multiplex RT-LAMP reaction without altering the sensitivity of the reaction. For POC use, the RT-LAMP assay may be performed using low-tech, portable heating devices, such as the ESEQuant Tube Scanner (Qiagen, Valencia, Calif.) or non-instrumented nucleic acid (NINA) heaters. Similar performance between these devices and traditional thermal cyclers has been demonstrated for a previous HIV-1 RT-LAMP assay (Curtis et al., PLoS ONE e:31432, 2012). In the current study, however, a thermal cycler was used as a matter of convenience for large-scale testing.

Because of the predominant use of rapid tests in non-laboratory settings, a representative rapid test was used as the primary basis for comparison to the HIV-1 RT and INT RT-LAMP assays. The antibody-based Multispot HIV-1/HIV-2 Rapid Test was selected for comparison, given that it is currently used as a supplemental assay in the laboratory testing algorithm. It should be noted, however, that the Multispot is not currently Clinical Laboratory Improvement Amendments (CLIA)-waived for use at the POC. In seroconverting individuals, the assays described herein demonstrated earlier detection (1-3 weeks) with the RT-LAMP assay as compared to the Multispot HIV-1/HIV-2 Rapid Test. Furthermore, studies have demonstrated that the Multispot and other FDA-approved rapid tests show significant weaknesses in detecting early HIV infection (Louie et al., J. Clin. Microbiol. 44:1856-1858, 2006; Patel et al., J. Clin. Virol. 54:42-47, 2012). Since RT-LAMP can be performed in about an hour without costly equipment requirements, the rapid NAAT may fill the gap in testing needs at clinics or low-resource testing sites. Used in conjunction with current commercial rapid tests, the HIV-1 RT-LAMP assay has the potential to reduce the numbers of individuals that require follow-up laboratory testing by confirming the presence of HIV nucleic acid at the time of the visit to the clinic/testing site.

Although the LAMP method is attractive for the development of a rapid POC NAAT, the HIV-1 RT-LAMP assay may also be useful in select laboratory settings, because of the quicker turnaround time and lower cost compared to current laboratory NAAT platforms. In relation to the viral load for each seroconversion panel member, RT-LAMP exhibited the expected limit of detection for the assay, which is approximately $10^4$ RNA copies/ml. Additionally, RT-LAMP had a slight or no delay in time to detection compared to the current FDA-approved NAAT (APTIMA) in the seroconverting individuals. The viral loads of all seroconverters included in this study exceeded the limit of detection for the assay shortly post first RNA-positive test result.

At present, the fourth-generation immunoassay is the most sensitive of the laboratory platforms, since it detects anti-HIV-1 IgG and IgM antibodies and HIV-1 p24 antigen. Rapid fourth-generation tests, such as the Determine HIV-1/2 Ag/Ab Combo (Alere, Orlando, Fla.) (Faraoni et al., *J. Clin. Virol.* 57:84-87, 2013; Brauer et al., *J. Virol. Meth.* 189:180-183, 2013; Masciotra et al., *J. Clin. Virol.* 58:e54-58, 2013) will likely soon be CLIA-waived for use at the POC, but data suggest that it is not as sensitive for detection of acute infection as laboratory platforms (Masciotra et al., *J. Clin. Virol.* 58:e54-58, 2013; Beelaert et al., *J. Virol. Meth.* 168:218-222, 2010; Fox et al., *Sexually transmitted infections* 87:178-179, 2011; Taegtmeyer et al., *PLoS ONE* 6:e28019, 2011; Chetty et al., *J. Clin Virol.* 54:180-184, 2012; Jones et al., *J. Inf. Dis.* 206:1947-1949; author reply 1949-1950, 2012; Kilembe et al., *PLoS ONE* 7:e37154, 2012; Laperche et al., *J. Inf. Dis.* 206:1946-1947; author reply 1949-1950, 2012; Rosenberg et al., *J. Inf. Dis.* 205: 528-534, 2012). Although p24 antigen narrows the window from infection to detection, nucleic acid remains the earliest detectable biomarker for HIV infection (Branson et al., *J. Inf. Dis.* 205:521-524, 2012). In support of this, the RT-LAMP assays disclosed herein detected infection up to two weeks earlier than the GS HIV Combo Ag/Ab EIA.

One of the weaknesses of the RT-LAMP assay is that the current format is not as sensitive as the APTIMA HIV-1 RNA Qualitative Assay, the only FDA-approved NAAT for HIV-1 diagnosis. In the current study, the APTIMA detected infection up to five days earlier than the RT-LAMP assay. However, without being bound by theory, it is believed that this is due to the large discrepancy in input sample volume between the two assays. When taking into account the extraction process that occurred prior to adding sample to the reaction, the RT-LAMP assays described herein used only 7% of the sample volume required for APTIMA. It has been demonstrated that the sensitivity of the RT-LAMP assay can be increased by increasing the overall reaction volume (Curtis et al., *J. Virol. Meth.* 151:264-270, 2008). In addition, HIV nucleic acids can be concentrated directly from the clinical specimen through membrane capture/concentration methods (Liu et al., *The Analyst* 136:2069-2076, 2011; Jangam et al., *Biosensors & Bioelectronics* 42:69-76-5, 2013). Furthermore, the APTIMA qualitative RNA assay takes several hours with multiple hands-on steps and requiring multiple pieces of equipment, making it much less suitable for POC use than the RT-LAMP assays described above.

Example 2

Detection of HIV-1 Nucleic Acids in Viral Diversity Panel

This example describes detection of HIV-1 nucleic acids in a viral diversity panel by RT-LAMP assay using group M-conserved primers.

RT-LAMP was performed on RNA isolated from samples from the EQAPOL viral diversity panel (External Quality Assurance Program Oversight Laboratory, Durham, N.C.). Viral RNA was extracted from each isolate and quantitative panels were created based on the viral load of each virus stock. RT-LAMP was performed with INT primers as described in Example 1. A multiplex of primers SEQ ID NOs: 8, 9, 12-23, 25, and 27 was used in the assay. The total amount of each type of primer added to the reaction mix was the same as described in Example 1. For example, if there are three versions of one type of primer, each primer was added at ⅓ the total concentration. Each panel member was tested in duplicate. Results are shown in Table 5. This assay detected all isolates, regardless of subtype, and detected the majority of the isolates in the sensitivity range of the assay.

TABLE 5

HIV-1 INT RT-LAMP primers with EQAPOL HIV-1 isolates

| Virus Name | Subtype | $10^{-7}$ | $10^{-6}$ | $10^{-5}$ | $10^{-4}$ | $10^{-3}$ |
|---|---|---|---|---|---|---|
| DE00109CN003.S1-AE | CRF01_AE | + + | + + | + + | + | |
| DE00109CN004.S1-AE | CRF01_AE | + + | + + | + + | + | |
| DE00110CN001.S1-AE | CRF01_AE | + + | + + | + + | + + | |
| DE00111CN002.S1-AE | CRF01_AE | + + | + + | + + | + + | |
| DE00206AO001.S1-AG | CRF02_AG | + + | + + | + + | + + | |
| DE00208CM001.S1-AG | CRF02_AG | + + | + + | + + | + + | |
| DE00208CM004.S1-AG | CRF02_AG | + + | + + | + + | + + | + |
| DEMA07UG005.S1-A1 | A1 | + + | | | | |
| DEMA11KE001.S1-A1 | A1 | + + | + + | + + | + | |
| DEMA106ES002.S1-A1 | A1 | + + | + + | + + | + + | |
| DEMA108RU003.S1-A1 | A1 | + + | + + | + + | + + | |
| DEMC07BR003.S1-C | C | + + | + + | + + | + + | + |
| DEMC07ZA011.S1-C | C | + + | + + | + + | + + | + |
| DEMC08NG001.S1-C | C | + + | + + | + + | + + | + + |
| DEMC08ZA011.S1-C | C | + + | + + | + + | + + | + |
| DEMD07UG007.S1-D | D | + + | + + | + + | + + | + |
| DEMD08UG001.S1-D | D | + + | + + | + + | + + | + |
| DEMD10CM009.S1-D | D | + + | + + | + + | + + | + |
| DEMD10UG004.S1-D | D | + + | + + | + + | + + | + |
| DEMF110ES001.S1-F1 | F1 | + + | + + | + + | + | |
| DEMF210CM001.S1-F2 | F2 | + + | + + | + + | | |
| DEMG05ES001.S1-G | G | + + | + + | + + | + + | |
| DEMG09ES002.S1-G | G | + + | + + | + | | |
| DEMG10CM008.S1-G | G | + + | + + | + + | | |

TABLE 5-continued

HIV-1 INT RT-LAMP primers with EQAPOL HIV-1 isolates

| Virus Name | Subtype | 10^7 | | 10^6 | | 10^5 | | 10^4 | | 10^3 |
|---|---|---|---|---|---|---|---|---|---|---|
| DEURF09GQ001.S1-URF | ADG (URF) | + | + | + | + | + | + | + | + | + |
| DEURF10DZ001.S1-URF | CRF02_AG/ CRF06_cpx (URF) | + | + | + | + | + | + | + | + | |

+, positive;
blank cells are considered to be negative.

Example 3

Detection of HIV-1 Nucleic Acids Using HIV-1 RT-LAMP

This example describes particular methods for detecting HIV-1 nucleic acid in a sample using an RT-LAMP assay. However, one skilled in the art will appreciate that methods that deviate from these specific methods can also be used to successfully detect HIV-1 nucleic acids in a sample.

Clinical samples are obtained from a subject (such as a subject suspected of having an HIV-1 infection), such as a whole blood or plasma sample. Typically, the sample is used directly or with minimal processing (for example, dilution in water or buffer at 1:2 to 1:10). However, RNA can be extracted from the sample using routine methods (for example using a commercial kit) if desired.

RT-LAMP is performed in a reaction including a reaction mix (e.g., buffers, MgCl$_2$, dNTPs, reverse transcriptase, and DNA polymerase), sample (10 µl of sample or 10 µl of nucleic acid extracted from the sample), and primers. The primers are included in the reaction as follows: F3 (SEQ ID NO: 8) and B3 (SEQ ID NO: 9) at 0.2 µM, FIP (SEQ ID NO: 10) and BIP (SEQ ID NO: 11) at 1.6 µM, Loop F (SEQ ID NO: 12) and Loop B (SEQ ID NO: 13 with 5' HEX) at 0.8 µM, and quencher (SEQ ID NO: 14 with 3' BHQ1) at 0.8 µM. Alternatively, the primers are included in the reaction as follows: F3 (SEQ ID NO: 8) at 0.2 µM; B3 (SEQ ID NOs: 9 and 15) at a total concentration of 0.2 µM (0.1 µM each); FIP (SEQ ID NOs: 16 and 17) at a total concentration of 1.6 µM (0.8 µM each); BIP (SEQ ID NOs: 18 and 19) at a total concentration of 1.6 µM (0.8 µM each); Loop F (SEQ ID NOs: 12 and 20) at 0.8 µM (0.4 µM each); Loop B (SEQ ID NOs: 13, 21, and 22, each with 5' HEX) at 0.8 µM (0.27 µM each); and quencher (SEQ ID NOs: 23 and 27 each with 3' BHQ1) at 0.8 µM (0.4 µM each). Optionally, any one of SEQ ID NOs: 10, 11, and 27 can also be included, if so, the total amount of the particular primer type in the reaction is maintained.

The assay is incubated at 60° C. for about 1 hour and the reaction is terminated by incubation at 80° C. for about 2 minutes. Samples are examined visually under an ultraviolet lamp. Positive samples are those with observable fluorescence greater than that in a reagent only (no sample) control tube. One of ordinary skill in the art will understand that other methods of detection can also be used, for example, a microfluidic platform with a visual readout.

Example 4

Multiplex HIV-1 RT-LAMP Assay for Detecting HIV-1 Nucleic Acids

This example describes particular methods for a multiplex RT-LAMP assay for detecting HIV-1 nucleic acids in a sample. However, one skilled in the art will appreciate that methods that deviate from these specific methods can also be used to successfully detect HIV-1 nucleic acids in a sample.

Clinical samples are obtained from a subject (such as a subject suspected of having an HIV-1 infection), such as a whole blood or plasma sample. Typically, the sample is used directly or with minimal processing. However, RNA can be extracted from the sample using routine methods (for example using a commercial kit) if desired.

RT-LAMP is performed in a reaction including a reaction mix (e.g., buffers, MgCl$_2$, dNTPs, betaine, reverse transcriptase, and DNA polymerase), sample (10 µl of sample or 10 µl of nucleic acid extracted from the sample), and primers. The HIV-1 INT primers are included in the reaction as described in Example 3 except at one-half the concentration and the HIV-1 RT primers are included as follows: F3 (SEQ ID NO: 1) and B3 (SEQ ID NO: 2) at 0.1 µM, HP (SEQ ID NO: 3) and BIP (SEQ ID NO: 4) at 0.8 µM, Loop F (SEQ ID NO: 5 with 5' HEX) and Loop B (SEQ ID NO: 6) at 0.4 µM, and quencher (SEQ ID NO: 7 with 3' BHQ1) at 0.4 µM. The assay is incubated at 60° C. for about 1 hour and the reaction is terminated by incubation at 80° C. for about 2 minutes. Samples are examined visually under an ultraviolet lamp. Positive samples are those with observable fluorescence greater than that in a reagent only (no sample) control tube.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of detecting presence of human immunodeficiency virus-1 (HIV-1) nucleic acid in a sample, comprising:
contacting the sample with at least one set of loop-mediated isothermal amplification (LAMP) primers specific for an HIV-1 integrase nucleic acid under conditions sufficient for amplification of the HIV-1 integrase nucleic acid, thereby producing an HIV-1 integrase nucleic acid amplification product,
wherein the at least one set of LAMP primers specific for the HIV-1 integrase nucleic acid comprises each of:
a forward outer primer (F3),
a backward outer primer (B3),
a forward inner primer (FIP),
a backward inner primer (BIP),
a forward loop primer (Loop F), and
a backward loop primer (Loop B); and
wherein the at least one set of LAMP primers specific for the HIV-1 integrase nucleic acid are selected from nucleic acid sequences comprising a sequence at least 90% identical to a sequence selected from SEQ ID NOs: 8-13 and 15-22; and
detecting the HIV-1 integrase nucleic acid amplification product, thereby detecting presence of HIV-1 nucleic acid in the sample.

2. The method of claim 1, wherein the at least one set of LAMP primers is specific for a Group M HIV-1 integrase nucleic acid.

3. The method of claim 1, wherein the at least one set of LAMP primers specific for an HIV-1 integrase nucleic acid comprises primers comprising a nucleic acid sequence at least 90% identical to each of SEQ ID NOs: 8-13.

4. The method of claim 3, wherein the set of LAMP primers comprises primers comprising the nucleic acid sequence of each of SEQ ID NOs: 8-13.

5. The method of claim 4, wherein the set of LAMP primers comprises primers consisting of the nucleic acid sequence of each of SEQ ID NOs: 8-13.

6. The method of claim 3, wherein the at least one set of LAMP primers specific for an HIV-1 integrase nucleic acid further comprises one or more primers comprising a nucleic acid sequence at least 90% identical to any one of SEQ ID NOs: 15-22.

7. The method of claim 6, wherein the set of LAMP primers comprises one or more primers comprising the nucleic acid sequence of any one of SEQ ID NOs: 15-22.

8. The method of claim 7, wherein the set of LAMP primers comprises one or more primers consisting of the nucleic acid sequence of any one of SEQ ID NOs: 15-22.

9. The method of claim 1, wherein the at least one set of LAMP primers specific for an HIV-1 integrase nucleic acid comprises primers comprising a nucleic acid sequence at least 90% identical to each of SEQ ID NOs: 8, 9, 12-13, and 15-22.

10. The method of claim 9, wherein the set of LAMP primers comprises primers comprising the nucleic acid sequence of each of SEQ ID NOs: 8, 9, 12-13, and 15-22.

11. The method of claim 10, wherein the set of LAMP primers comprises primers consisting of the nucleic acid sequence of each of SEQ ID NOs: 8, 9, 12-13, and 15-22.

12. The method of claim 1, wherein at least one primer in the set of LAMP primers comprises a detectable label.

13. The method of claim 12, wherein the detectable label comprises a fluorophore.

14. The method of claim 1, wherein the at least one set of LAMP primers further comprises at least one quencher oligonucleotide.

15. The method of claim 14, wherein the at least one quencher oligonucleotide comprises the nucleic acid sequence of any one of SEQ ID NOs: 14 and 23-27 and a fluorescence quencher.

16. The method of claim 15, wherein the at least one quencher oligonucleotide consists of the nucleic acid sequence of any one of SEQ ID NOs: 14 and 23-27 and the fluorescence quencher.

17. The method of claim 1, further comprising:
contacting the sample with at least one set of loop-mediated isothermal amplification (LAMP) primers specific for an HIV-1 reverse transcriptase nucleic acid under conditions sufficient for amplification of the HIV-1 reverse transcriptase nucleic acid, thereby producing an HIV-1 reverse transcriptase amplification product; and
detecting the HIV-1 reverse transcriptase amplification product.

18. The method of claim 17, wherein the at least one set of LAMP primers specific for an HIV-1 reverse transcriptase nucleic acid comprises primers comprising a nucleic acid sequence at least 90% identical to each of SEQ ID NOs: 1-6.

19. The method of claim 18, wherein the set of LAMP primers comprises primers comprising the nucleic acid sequence of each of SEQ ID NOs: 1-6.

20. The method of claim 19, wherein the set of LAMP primers comprises primers consisting of the nucleic acid sequence of each of SEQ ID NOs: 1-6.

21. The method of claim 17, wherein at least one primer in the set of LAMP primers specific for reverse transcriptase nucleic acid comprises a detectable label.

22. The method of claim 21, wherein the detectable label comprises a fluorophore.

23. The method of claim 17, wherein the at least one set of LAMP primers specific for the HIV-1 reverse transcriptase nucleic acid further comprises a quencher oligonucleotide.

24. The method of claim 23, wherein the quencher oligonucleotide comprises the nucleic acid sequence of SEQ ID NO: 7 and a fluorescence quencher.

25. The method of claim 24, wherein the quencher oligonucleotide consists of the nucleic acid sequence of SEQ ID NO: 7 and the fluorescence quencher.

26. The method of claim 23, wherein the quencher oligonucleotide comprises a dark quencher.

27. The method of claim 1, further comprising contacting the sample with a reverse transcriptase under conditions sufficient for reverse transcription of the HIV-1 nucleic acid.

28. The method of claim 1, wherein detecting the HIV-1 amplification product comprises turbidity measurement, fluorescence detection, or gel electrophoresis.

29. The method of claim 1, wherein the sample comprises isolated DNA, isolated RNA, blood, urine, saliva, tissue biopsy, fine needle aspirate, or a surgical specimen.

30. The method of claim 1, wherein the at least one set of LAMP primers specific for an HIV-1 integrase nucleic acid comprises sequences comprising each of SEQ ID NOs: 8-14.

31. The method of claim 1, wherein the at least one set of LAMP primers specific for an HIV-1 integrase nucleic acid comprises sequences comprising each of SEQ ID NOs: 8, 9, 12-23, and 25.

32. An isolated nucleic acid primer comprising the nucleic acid sequence of any one of SEQ ID NOs: 10, 11, 16, 17, 18, and 19.

33. The isolated nucleic acid primer of claim 32, consisting of the nucleic acid sequence of any one of SEQ ID NOs: 10, 11, 16, 17, 18, and 19.

34. The isolated nucleic acid primer of claim 32, further comprising a detectable label or a fluorescent quencher.

35. A kit comprising a set of isolated nucleic acid primers specific for an HIV-1 integrase nucleic acid, comprising:
   primers comprising the nucleic acid sequence of each of SEQ ID NOs: 8-14; or
   primers comprising the nucleic acid sequence each of SEQ ID NOs: 8, 9, 12-23, and 25.

* * * * *